United States Patent [19]
Falco et al.

[11] Patent Number: 5,912,414
[45] Date of Patent: Jun. 15, 1999

[54] NUCLEIC ACID FRAGMENTS, CHIMERIC GENES AND METHODS FOR INCREASING THE METHIONINE CONTENT OF THE SEEDS OF PLANTS

[75] Inventors: Saverio Carl Falco, Arden; Anthony Dominick Guida, Jr., Newark, both of Del.; Mary Elizabeth Hartnett Locke, Glassboro, N.J.

[73] Assignee: E. I. du Pont de Nemours and Company, Wilmington, Del.

[21] Appl. No.: 08/737,524

[22] PCT Filed: May 12, 1995

[86] PCT No.: PCT/US95/05545

§ 371 Date: Nov. 8, 1996

§ 102(e) Date: Nov. 8, 1996

[87] PCT Pub. No.: WO95/31554

PCT Pub. Date: Nov. 23, 1995

Related U.S. Application Data

[63] Continuation-in-part of application No. 08/242,408, May 13, 1994, abandoned.

[51] Int. Cl.$^6$ .............................. A01H 5/00; A01H 5/10; C12N 1/21; C12N 5/14; C12N 9/00; C12N 15/29; C12N 15/52; C12N 15/82

[52] U.S. Cl. ....................... 800/205; 435/172.3; 435/183; 435/252.3; 435/320.1; 435/419; 536/23.2; 536/23.6; 800/250

[58] Field of Search .................................. 536/23.2, 23.6, 536/23.7; 435/172.3, 320.1, 183, 419, 252.3; 800/205, 250

[56] References Cited

FOREIGN PATENT DOCUMENTS

WO 92/14822  9/1992  WIPO ............................ C12N 15/29
WO 93/19190  9/1993  WIPO ............................ C12N 15/82

OTHER PUBLICATIONS

Stam M, et al. "The silence of genes in transgenic plants." Ann. Bot. 79: 3–12, 1997.

Koziel MG, et al. "Optimizing expression of transgenes with an emphasis on post–transcriptional events." Plant Mol. Biol. 32: 393–405 1996.

Smith CJS, et al. "Antisense RNA inhibition of polygalacturonase gene expression in transgenic tomatoes." Nature 334: 724–726, Aug. 25, 1988.

Kreft, B. D. et al, *Plant Physiol.*, 104, 1215–1220, 1994.

Thompson, G.A. et al, *Plant. Physiol.*, 69, 1077–1083, 1982.

Datko, A. H., *The Journal of Biological Chemistry*, 249(4), 1139–1155, 1974.

Phillips, R. L. et al, *Cereal Chem.*, 62, 213–218, 1985.

Madison, J.T. & Thompson, J.F., *Plant Cell Reports*, 7, 473–476, 1988.

Giovanelli, J. et al, *Plant Physiol.*, 77, 450–455, 1984.

Duchange, N, et al, *The Journal of Biological Chemistry*, 258(24), 14868–14871, 1983.

Altenbach, S.B. et al, *Plant Molecular Biology*, 18, 235–245, 1992.

Altenbach, S.B. et al, *Plant Molecular Biology*, 13, 513–522, 1989.

Hoffman, L.M. et al, *The EMBO Journal*, 6(11), 3213–3221, 1987.

Rafalski, J.A. et al, *The Journal of Biological Chemistry*, 263(5), 2146–2151 (1988).

Cassan M., *The Journal of Biological Chemistry*, 261(3), 1052–1057, 1966.

Katinka, M. et al, *Proc. Natl. Acad. Sci. USA*, 77(10), 5730–5733, Oct. 1980.

Zakin, M.M. et al, *The Journal of Biological Chemistry*, 285(5), 3028–3031, 1983.

Le Guen, L. et al., Structure and expression of a gene from *Arabidopsis thaliana* encoding a protein related to SNF1 protein kinase, *Gene*, 120, 249–254, 1992.

EMBL Sequence Database Acc. No. D24443, Rel. 37, Nov. 29, 1993.

EMBL Sequence Database Acc. No. Z18176, Rel. 33, Nov. 6, 1992.

Le Guen, L. et al., Gene density and organization in a small region of the *Arabidopsis thaliana* genome, *Molecular and General Genetics*, 245, 390–396, 1994.

Kreft, B. D. et al., Purification and Properties of Cystathionine γ–Synthase from Wheat (*Triticum aestivum* L.), *Plant Physiology*, 104, 1215–1220, 1994.

Duchange, N. et al., Structure of the metJBLF Cluster in *Escherichia coli* K12, *The Journal of Biological Chemistry*, 258, 14868–14871, 1983.

Saito, K. et al., Molecular cloning and bacterial expression cDNA encoding a plant cysteine synthase, *Proceedings of National Academy of Sciences, USA*, 89, 8078–8082, 1992.

Youssefian, S. et al., Tobacco plants transformed with the O–acetylserine (thiol) lyase gene of wheat are resistant to toxic levels of hydrogen sulphide gas, *The Plant Journal*, 4(5), 759–769, 1993.

(List continued on next page.)

*Primary Examiner*—Douglas W. Robinson
*Assistant Examiner*—Amy J. Nelson

[57] ABSTRACT

Four chimeric genes are disclosed. A first chimeric gene encoding a plant cystathionine γ-synthase (CS), a second chimeric gene encoding feedback-insensitive aspartokinase, which is operably linked to a plant chloroplast transit sequence, a third chimeric gene encoding bifunctional feedback-insensitive aspartokinase-homoserine dehydrogenase (AK-HDH), which is operably linked to a plant chloroplast transit sequence, and a fourth chimeric gene encoding a methionine-rich protein, all operably linked to plant seed-specific regulatory sequences are discussed. Methods for their use to produce increased levels of methionine in the seeds of transformed plants are provided.

37 Claims, 2 Drawing Sheets

OTHER PUBLICATIONS

Falco, S. C. et al., Transgenic Crops With Improved Amino Acid Composition, *Journal of Cellular Biochemistry Supplement*, 18A, 79, 1994 & *Keystone Symposium on Improved Crop and Plant Products Through Biotechnology,* Keystone, Colorado, USA, Jan. 9–16, 1994.

Karchi, H. et al., Seed–specific expression of a bacterial desensitized aspartate kinase increases the production of seed threonine and methionine in transgenic tobacco, *The Plant Journal,* 3(5), 721–727, 1993.

Kirihara, J. A. et al., A Transgenic Corn Line With Altered Levels Of A High–Methionine Storage Protein, *Journal of Cell Biochemicstry Suppl. Symposium,* 16F, 225, Apr. 10–16, 1992, Abstr. Y304.

Park, J. W. et al., Promoter Sequence of Soybean Glycinin Gene Regulates Seed–Specific Expression in Transgenic Tobacco Plant, *Mol. Cells,* 2, 297–302, 1992.

Kim, J. et al., Cloning and analysis of the gene for cystathionine γ–synthase from *Arabidopsis thaliana, Plant Molecular Biology,* 32, 1117–1124, 1996.

```
 89 LLGSDASLAVHAGERLGRRIATDAITTPVVNTSAYWFNNSQELIDFKEKEGR 138  Corn CS
    : .:|.::||:.|  |. . :.:.:|: .|.|    ::.:|.|.|
  1 MTRKQATIAVRSG..LNDDEQYGCVVPPIHLSSTY......NFTGFNEPR   42  E. coli CS 139 HASFEYGRYGNPTTEALEKKMSALEKAESTVFVASGMYAAVAMLSALVPA  188  Corn CS
      .  :|||  ||||  :::.:|:: ..:|::..||  |   :  ::::
 43 ..AHDYSRRGNPTRDVVQRALAELEGGAGAVLTNTGMSAIHLVTTVFLKP   90  E. coli CS 189 GGHIVTTTDCYRKTRIYMENELPKRGI.SMTVIRPADMDALQNALDNNNV 237  Corn CS
    |:  :|.. |||    ...: :.|:|||.  .:  .:|  :||..||. :..
 91 GDLLVAPHDCY.GGSYRLFDSLAKRGCYRVLFVDQGDEQALRAALA.EKP 138  E. coli CS 238 SLFFTETPTNPFLRCIDIEHVSNMCHSKGALLCIDSTFASPINQKALTLG 287  Corn CS
    .|.:.|.|.|..|:.:|| .::|| .     ||:   .:|.:|| ||   |.:.|||
139 KLVLVESPSNPLLRVVDIAKICHLAREVGAVSVVDNTFLSPALQNPLALG 188  E. coli CS 288 ADLVIHSATKYIAGHNDVIGGCVSGRD.ELVSKVRIYHHVVGGVLNPNAA 336  Corn CS
    ||||:||::||. ||.|||||.:|.|  :||  |.:| ..:| .|: . :..
189 ADLVLHSCTKYLNGHSDVVAGVVIAKDPDVVTELAWWANNIGVTGGAFDS 238  E. coli CS 337 YLILRGMKTLHLRVQCQNDTALRMAQFLEEHPKIARVYYPGLPSHPEHHI 386  Corn CS
    ||:|||::||  |:|   ..  .|  .|      |.:|::|.::|:::|.|
239 YLLRGLRTLVPRMELAQRNAQAIVKYLQTQPLVKKLYHPSLPENQGHEI   288  E. coli CS 387 AKSQMTGFGGVSFEVAGDFDATRKFIDSVKIPYHAPSFGGCESIIDQPA  436  Corn CS
    |  .|   |:.||||:|::|::..||  .:  |:|::..:|  ..:|:::|
289 AARQQKGFGAMLSFELDGDEQTLRRFLGGLSLFTLAESLGGVESLISHAA 338  E. coli CS 437 IMSYWD.SKEQRDIYGIKDNLIRFSIGVEDFEDLKNDLVQALEKI       480  Corn CS
    .|. ..:| . ||.:|::.::::|::|| |||   .|:
339 TMTHAGMAPEARAAAGISETLLRISTGIEDGEDLIADLENGFRAANKG    386  E. coli CS
```

FIG. 1

NUCLEIC ACID FRAGMENTS, CHIMERIC GENES AND METHODS FOR INCREASING THE METHIONINE CONTENT OF THE SEEDS OF PLANTS

CROSS REFERENCE TO RELATED APPLICATION

This is a continuation-in-part of application Ser. No. 08/242,408, filed May 13, 1994, now abandoned.

TECHNICAL FIELD

This invention relates to four chimeric genes, a first encoding a plant cystathionine γ-synthase (CS), a second encoding feedback-insensitive aspartokinase, which is operably linked to a plant chloroplast transit sequence, a third encoding bifunctional feedback-insensitive aspartokinase-homoserine dehydrogenase (AK-HDH), which is operably linked to a plant chloroplast transit sequence, and a fourth encoding a methionine-rich protein, all operably linked to plant seed-specific regulatory sequences. Methods for their use to produce increased levels of methionine in the seeds of transformed plants are provided.

BACKGROUND OF THE INVENTION

Human food and animal feed derived from many grains are deficient in the sulfur amino acids, methionine and cysteine, which are required in an animal diet. In corn, the sulfur amino acids are the third most limiting amino acids, after lysine and tryptophan, for the dietary requirements of many animals. The use of soybean meal, which is rich in lysine and tryptophan, to supplement corn in anmial feed is limited by the low sulfur amino acid content of the legume. Thus, an increase in the sulfur amino acid content of either corn or soybean would improve the nutritional quality of the mixtures and reduce the need for further supplementation through addition of more expensive methionine.

Efforts to improve the sulfur amino acid content of crops through plant breeding have met with limited success on the laboratory scale and no success on the commercial scale. A mutant corn line which had an elevated whole-kernel methionine concentration was isolated from corn cells grown in culture by selecting for growth in the presence of inhibitory concentrations of lysine plus threonine [Phillips et al. (1985) Cereal Chem. 62:213–218]. However, agronomically-acceptable cultivars have not yet been derived from this line and commercialized. Soybean cell lines with increased intracellular concentrations of methionine were isolated by selection for growth in the presence of ethionine [Madison and Thompson (1988) Plant Cell Reports 7:472–476], but plants were not regenerated from these lines.

The amino acid content of seeds is determined primarily by the storage proteins which are synthesized during seed development and which serve as a major nutrient reserve following germination. The quantity of protein in seeds varies from about 10% of the dry weight in cereals to 20–40% of the dry weight of legumes. In many seeds the storage proteins account for 50% or more of the total protein. Because of their abundance, plant seed storage proteins were among the first proteins to be isolated. Only recently, however, have the amino acid sequences of some of these proteins been determined with the use of molecular genetic techniques. These techniques have also provided information about the genetic signals that control the seed-specific expression and the intracellular targeting of these proteins.

One genetic engineering approach to increase the sulfur amino acid content of seeds is to isolate genes coding for proteins that are rich in the sulfur-containing amino acids methionine and cysteine, to link the genes to strong seed-specific regulatory sequences, to transform the chimeric gene into crops plants and to identify transformants wherein the gene is sufficiently-highly expressed to cause an increase in total sulfur amino acid content. However, increasing the sulfur amino acid content of seeds by expression of sulfur-rich proteins may be limited by the ability of the plant to synthesize methionine, by the synthesis and stability of the methionine-rich protein, and by effects of over-accumulation of the methionine-rich protein on the viability of the transgenic seeds.

An alternative approach would be to increase the production and accumulation of the free amino acid, methionine, via genetic engineering technology. However, little guidance is available on the control of the biosynthesis and metabolism of methionine in plants, particularly in the seeds of plants.

Methionine, along with threonine, lysine and isoleucine, are amino acids derived from aspartate. The first step in the pathway is the phosphorylation of aspartate by the enzyme aspartokinase (AK), and this enzyme has been found to be an important target for regulation of the pathway in many organisms. The aspartate family pathway is also believed to be regulated at the branch-point reactions. For methionine the reduction of aspartyl β-semialdehyde by homoserine dehydrogenase (HDH) may be an important point of control. The first committed step to methionine, the production of cystathionine from O-phosphohomoserine and cysteine by cystathionine γ-synthase (CS), appears to be the primary point of control of flux through the methionine pathway [Giovanelli et al. (1984) Plant Physiol. 77:450–455].

Before the present invention, no plant gene encoding CS was available for use in genetically engineering the methionine biosynthetic pathway. The present invention provides chimeric CS genes for seed-specific over-expression of the plant enzyme. Combinations of these genes with other chimeric genes encoding AK or AK-HDH and methionine-rich seed storage protein provide methods to increase the level of methionine in seeds.

SUMMARY OF THE INVENTION

Disclosed herein are four chimeric genes, a first encoding a plant cystathionine γ-synthase (CS), a second encoding lysine-insensitive aspartokinase (AK), which is operably linked to a plant chloroplast transit sequence, a third encoding bifunctional feedback-insensitive aspartokinase-homoserine dehydrogenase (AK-HDH), which is operably linked to a plant chloroplast transit sequence, and a fourth encoding a methionine-rich protein, all chimeric genes operably linked to plant seed-specific regulatory sequences.

The invention includes an isolated nucleic acid fragment encoding a corn cystathionine γ-synthase.

Also included herein is an isolated nucleic acid fragment comprising:

(a) a first nucleic acid fragment encoding a plant cystathionine γ-synthase; and (b) a second nucleic acid fragment encoding aspartokinase which is insensitive to end-product inhibition. Also disclosed is this isolated fragment wherein either the first nucleic acid fragment is derived from corn or wherein the second nucleic acid fragment comprises a nucleotide sequence essentially similar to the sequence shown in SEQ ID NO:4 encoding *E. coli* AKIII, said nucleic acid fragment encoding a lysine-insensitive variant of *E. coli* AKIII and further characterized in that at least one of the following conditions is met:
(1) the amino acid at position 318 is an amino acid other than methionine, or
(2) the amino acid at position 352 is an amino acid other than threonine.

Further disclosed herein is an isolated nucleic acid fragment comprising
(a) a first nucleic acid fragment encoding a plant cystathionine γ-synthase and
(b) a second nucleic acid fragment encoding a bi-functional protein with aspartokinase and homoserine dehydrogenase activities, both of which are insensitive to end-product inhibition. In one embodiment of this invention, this nucleic acid fragment has a first nucleic acid fragment derived from corn and in another the second nucleic acid fragment comprises a nucleotide sequence essentially similar to the *E. coli* metL gene.

Also disclosed is a nucleic acid fragment comprising a first chimeric gene wherein a nucleic acid fragment encoding a plant cystathionine γ-synthase is operably linked to a seed-specific regulatory sequence and a second chimeric gene wherein a nucleic acid fragment encoding aspartokinase, which is insensitive to end-product inhibition, is operably linked to a plant chloroplast transit sequence and to a seed-specific regulatory sequence. This invention also includes another nucleic acid fragment comprising this same first chimeric gene and a second chimeric gene wherein a nucleic acid fragment encoding a bi-functional protein with aspartokinase and homoserine dehydrogenase activities, both of which are insensitive to end-product inhibition, is operably linked to a plant chloroplast transit sequence and to a seed-specific regulatory sequence.

The invention also includes plants comprising in their genomes any of the the fragments or constructs herein described and their seeds.

The invention further includes a method for increasing the methionine content of plant seeds comprising:
(a) transforming plant cells with a first chimeric gene wherein a nucleic acid fragment encoding a plant cystathionine γ-synthase is operably linked to a seed-specific regulatory sequence;
(b) growing fertile mature plants from the transformed plant cells obtained from step (a) under conditions suitable to obtain seeds and
(c) selecting from the progeny seed of step (b) those seeds containing increased levels of methionine compared to untransformed seeds. The invention also includes tranforming plant cells in step (a) with a nucleic acid fragment with the same first chimeric gene and a second chimeric gene wherein a nucleic acid encoding apartokinase which is insensitive to end-product inhibition is operably linked to a plant chloroplast sequence and to a seed-specific regulatory sequence or transforming plant cells in step (a) with a nucleic acid fragment having the same first chimeric gene but also having a second chimeric gene wherein a nucleic acid fragment encoding a bi-functional protein with aspartokinase and homoserine dehydrogenase activities, both of which are insensitive to end-product inhibition, is operably linked to a plant chloroplast transit sequence and to a seed-specific regulatory sequence.

The invention includes plants and seeds having in their genomes any of the previously described first and second chimeric genes and a third chimeric gene wherein a nucleic acid fragment encoding a methionine-rich protein, wherein the weight percent methionine is at least 15%, is operably linked to a seed-specific regulatory sequence. Also disclosed is a nucleic acid fragment having the same first, second, and third chimeric genes. Also disclosed is a method for increasing the methionine content of the seeds of plants comprising transforming plant cells with this nucleic acid fragment; (b) growing fertile mature plants from the transformed plant cells obtained from step (a) under conditions suitable to obtain seeds; and (c) selecting from the progeny seed of step (b) those seeds containing increased levels of methionine compared to untransformed seeds.

Further disclosed herein is a chimeric gene wherein the nucleic acid fragment described on page 3, starting at line 19, is operably linked to a regulatory sequence capable of expression in microbial cells. Also disclosed is a method for producing plant cystathionine gamma synthase comprising:
(a) transforming a microbial host cell with that chimeric gene;
(b) growing the transformed microbial cells obtained from step (a) under conditions that result in the expression of plant cystathionine gamma synthase protein.

BRIEF DESCRIPTION OF THE DRAWINGS AND SEQUENCE DESCRIPTIONS

The invention can be more fully understood from the following detailed description and the accompanying drawings and the sequence descriptions which form a part of this application.

FIG. 1 shows a comparison of the amino acid sequences of part of the corn CS and *E. coli* CS proteins.

Figure 2:
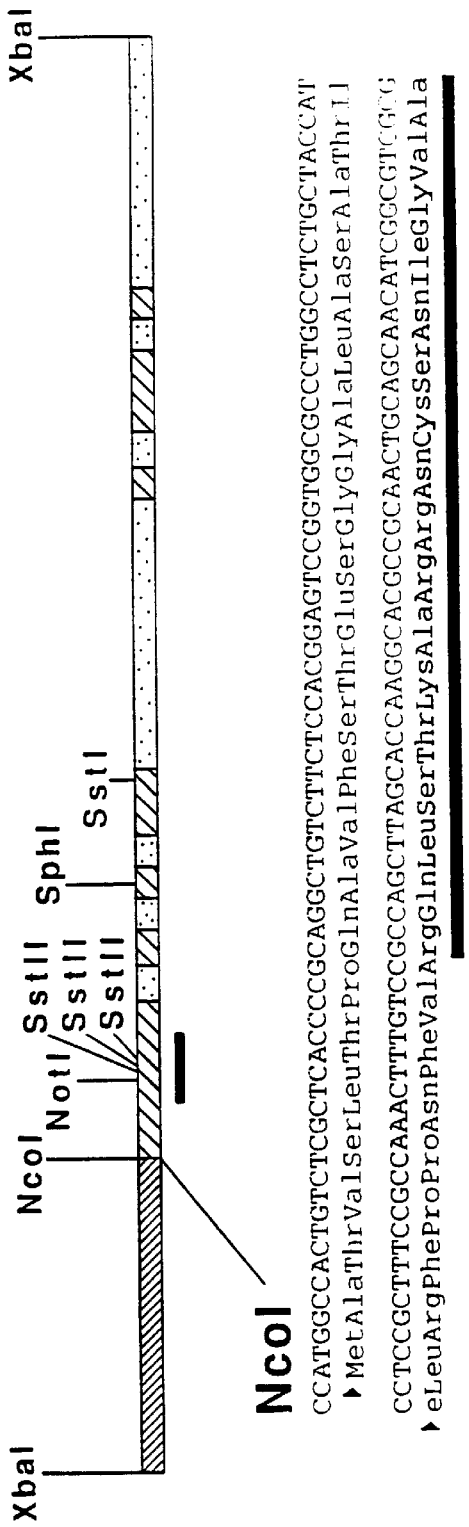
FIG. 2 shows a corn CS genomic DNA fragment, including 5' non-coding region, exons and introns. The nucleotide sequence and corresponding amino acid of the first exon is shown and a DNA segment that is deleted in a corn CS cDNA fragment is indicated.

SEQ ID NO:1 shows the nucleotide sequence of a corn CS cDNA and the corresponding amino acid sequence of the corn CS protein, described in Example 1.

SEQ ID NOS:2 and 3 show oligonucleotides used to add a translation initiation codon to the corn CS gene.

SEQ ID NO:4 shows the nucleotide and amino acid sequence of the coding region of the wild type *E. coli* lysC gene, which encodes AKIII, described in Example 3.

SEQ ID NOS:5 and 6 were used in Example 3 to create an Nco I site at the translation start codon of the *E. coli* lysC gene.

SEQ ID NOS:7 and 8 were used in Example 4 to screen a corn library for a high methionine 10 kD zein gene.

SEQ ID NO:9 shows the nucleotide sequence (2123 bp) of the corn HSZ gene and the predicted amino acid sequence of the primary translation product. Nucleotides 753–755 are the putative translation initiation codon and nucleotides 1386–1388 are the putative translation termination codon. Nucleotides 1–752 and 1389–2123 include putative 5' and 3' regulatory sequences, respectively.

SEQ ID NOS: 10 and 11 were used in Example 5 to modify the HSZ gene by in vitro mutagenesis.

SEQ ID NO:12 shows a 635 bp DNA fragment including the HSZ coding region only, which can be isolated by restriction endonuclease digestion using Nco I (5'-CCATGG) to Xba I (5'-TCTAGA). Two Nco I sites that were present in the native HSZ coding region were eliminated by site-directed mutagenesis, without changing the encoded amino acid sequence.

SEQ ID NOS: 13 and 14 were used in Example 5 to create a form of the HSZ gene with alternative unique restriction endonuclease sites.

SEQ ID NOS:15 and 16 were used in Example 5 to create a gene to code for the mature form of HSZ.

SEQ ID NO:17 shows a 579 bp DNA fragment including the coding region of the mature HSZ protein only, which can be isolated by restriction endonuclease digestion using BspH I (5'-TCATGA) to Xba I (5'-TCTAGA). Two Nco I sites that were present in the native HSZ coding region were eliminated by site-directed mutagenesis. This was accomplished without changing the encoded amino acid sequence.

SEQ ID NOS:18–23 were used in Example 6 to create a corn chloroplast transit sequence and link the sequence to the *E. coli* lysC-M4 gene.

SEQ ID NOS:24–25 were used in Example 7 as PCR primers to isolate and modify the *E. coli* metL gene.

SEQ ID NO:26 shows the nucleotide sequence and a 3639 bp Xba I corn genomic DNA fragment encoding two-thirds of the corn CS protein and including 806 bp upstream from the protein coding region as described in Example 1.

SEQ ID NO:27 shows the complete amino acid sequence of the corn CS protein deduced from the corn cDNA genomic DNA fragment of SEQ ID NO:1 and the corn genomic DNA fragment of SEQ ID NO:26.

The Sequence Descriptions contain the one letter code for nucleotide sequence characters and the three letter codes for amino acids as defined in conformity with the IUPAC-IYUB standards described in Nucleic Acids Research 13:3021–3030(1985) and in the Biochemical Journal 219 (No. 2):345–373(1984) which are incorporated by reference herein.

DETAILED DESCRIPTION OF THE INVENTION

The teachings below describe nucleic acid fragments, chimeric genes and procedures useful for increasing the accumulation of methionine in the seeds of transformed plants, as compared to levels of methionine in untransformed plants.

In the context of this disclosure, a number of terms shall be utilized. As used herein, the term "nucleic acid" refers to a large molecule which can be single-stranded or double-stranded, composed of monomers (nucleotides) containing a sugar, phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers.

As used herein, "essentially similar" refers to DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity of the encoded products. Moreover, the skilled artisan recognizes that "essentially similar" sequences encompassed by this invention are also defined by their ability to hybridize, under stringent conditions (0.1× SSC, 0.1% SDS, 65° C.), with the sequences exemplified herein.

"Gene" refers to a nucleic acid fragment that expresses a specific protein, including regulatory sequences preceding (5' non-coding) and following (3' non-coding) the coding region. "Native" gene refers to the gene as found in nature with its own regulatory sequences. "Chimeric" gene refers to a gene comprising heterogeneous regulatory and coding sequences. "Endogenous" gene refers to the native gene normally found in its natural location in the genome. A "foreign" gene refers to a gene not normally found in the host organism but that is introduced by gene transfer.

"Coding sequence" refers to a DNA sequence that codes for a specific protein and excludes the non-coding sequences.

"Initiation codon" and "termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript. "Messenger RNA" (mRNA) refers to RNA that can be translated into protein by the cell. "cDNA" refers to a double-stranded DNA one strand of which is complementary to and derived from mRNA by reverse transcription. "Sense" RNA refers to RNA transcript that includes the mRNA.

As used herein, "regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell. These regulatory sequences include promoters, translation leader sequences, transcription termination sequences, and polyadenylation sequences.

"Promoter" refers to a DNA sequence in a gene, usually upstream (5') to its coding sequence, which controls the expression of the coding sequence by providing the recognition for RNA polymerase and other factors required for proper transcription. A promoter may also contain DNA sequences that are involved in the binding of protein factors which control the effectiveness of transcription initiation in response to physiological or developmental conditions. It may also contain enhancer elements.

An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Organ-specific" or "development-specific" promoters as referred to herein are those that direct gene expression almost exclusively in specific organs, such as leaves or seeds, or at specific development stages in an organ, such as in early or late embryogenesis, respectively.

The term "operably linked" refers to nucleic acid sequences on a single nucleic acid molecule which are associated so that the function of one is affected by the other. For example, a promoter is operably linked with a structural gene (i.e., a gene encoding aspartokinase that is lysine-insensitive as given herein) when it is capable of affecting the expression of that structural gene (i.e., that the structural gene is under the transcriptional control of the promoter).

The term "expression", as used herein, is intended to mean the production of the protein product encoded by a gene. More particularly, "expression" refers to the transcription and stable accumulation of the sense (MRNA) or antisense RNA derived from the nucleic acid fragment(s) of the invention that, in conjuction with the protein apparatus of the cell, results in altered levels of protein product. "Antisense inhibition" refers to the production of antisense RNA transcripts capable of preventing the expression of the target protein. "Overexpression" refers to the production of a gene product in transgenic organisms that exceeds levels of production in normal or non-transformed organisms. "Altered levels" refers to the production of gene product(s) in transgenic organisms in amounts or proportions differ from that of normal or non-transformed organisms.

The "3' non-coding sequences" refers to the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

The "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Mature" protein refers to a post-translationally processed polypeptide without its targeting signal. "Precursor" protein refers to the primary product of translation of mRNA. A "chloroplast targeting signal" is an amino acid sequence which is translated in conjunction with a protein and directs it to the chloroplast. "Chloroplast transit sequence" refers to a nucleotide sequence that encodes a chloroplast targeting signal.

"End-product inhibition" or "feedback inhibition" refers to a biological regulatory mechanism wherein the catalytic activity of an enzyme in a biosynthetic pathway is reversibly reduced by binding to one or more of the end-products of the pathway when the concentration of the end-product(s) reaches a sufficiently high level, thus slowing the biosynthetic process and preventing over-accumulation of the end-product.

"Transformation" herein refers to the transfer of a foreign gene into the genome of a host organism and its genetically stable inheritance. Examples of methods of plant transformation include Agrobacterium-mediated transformation and particle-accelerated or "gene gun" transformation technology.

"Host cell" means the cell that is transformed with the introduced genetic material.

Isolation of a Plant CS Gene

In order to increase the accumulation of free methionine in the seeds of plants via genetic engineering, a gene encoding cystathionine γ-synthase (CS) was isolated from a plant for the first time. CS catalyzes the first reaction wherein cellular metabolites are committed to the synthesis of methionine and has been implicated to play a key role in the regulation of methionine biosynthesis. Regulation is not achieved through feedback inhibition of CS by any of the pathway end-products [Thompson et al. (1982) Plant Physiol. 69:1077–1083], however. Thus over-expression of CS is expected to increase flux through the methionine branch of the biosynthetic pathway, even when high levels of methionine are accumulated.

The availability of a plant CS gene is critical. Although bacterial CS genes, such as the *E. coli* metB gene [Duchange et al. (1983) J. Biol. Chem. 258:14868–14871], have been isolated, bacterial CS uses O-succinylhomoserine as a substrate, and has little or no activity with O-phosphorylhomoserine, the physiological precursor of methionine in plants [Datko et al. (1974) J. Biol. Chem. 249:1139–1155]. Since plants lack homoserine transsuccinylase and thus do not produce O-succinylhomoserine, the bacterial genes would have little utility in plants.

We teach that a plant CS gene can be isolated by complementation of an *E. coli* host strain bearing a metB mutation. Such a strain requires methionine for growth due to inactivation of the *E. coli* gene that encodes CS. Functional expression of the plant CS gene allows the strain to grow in the absence of methionine. A plant cDNA library is constructed in a suitable *E. coli* expression vector, introduced into the *E. coli* host, and clones able to grow in the absence of methionine are selected. The use of this approach to isolate a corn CS cDNA gene is presented in detail in Example 1. The nucleotide sequence of a corn CS cDNA is provided in SEQ ID NO:1. CS genes from other plants could be similarly isolated by functional complementation of an *E. coli* metB mutation. Alternatively, other plant CS genes, either as cDNAs or genomic DNAs, could be isolated by using the corn CS gene as a DNA hybridization probe. In Example 1 we demonstrate the isolation of a corn genomic DNA fragment, shown in SEQ ID NO:26.

Nucleic acid fragments carrying plant CS genes can be used to produce the plant CS protein in heterologous host cells. The plant CS protein so produced can be used to prepare antibodies to the protein by methods well-known to those skilled in the art. The antibodies are useful for detecting plant CS protein in situ in plant cells or in vivo in plant cell extracts. Additionally, the plant CS protein can be used as a target to design and/or identify inhibitors of the enzyme that may be useful as herbicides. This is desirable because CS represents a rate-limiting enzyme in an essential biochemical pathway. Furthermore, inhibition of methionine biosynthesis may have additional pleiotropic effects, since methionine is metabolized to S-adenosyl-methionine, which is used in many important cellular processes. Preferred heterologous host cells for production of plant CS protein are microbial hosts. Microbial expression systems and expression vectors containing regulatory sequences that direct high level expression of foreign proteins are well known to those skilled in the art. Any of these could be used to construct chimeric genes for production of plant CS. These chimeric genes could then be introduced into appropriate microorganisms via transformation to provide high level expression of plant CS. An example of high level expression of plant CS in a bacterial host is provided (Example 2).

Isolation of AK Genes

Over-expression of feedback-insensitive AK increases flux through the entire pathway of aspartate-derived amino acids even in the presence of high concentrations of the pathway end-products lysine, threonine and methionine. This increased flux provides more substrate for CS and increases the potential for methionine over-accumulation.

Provided herein is a unique nucleic acid fragment wherein a CS chimeric gene is linked to a chimeric gene for AK, which is insensitive to feedback-inhibition by end-products of the biosynthetic pathway. Also provided is a unique nucleic acid fragment wherein a CS chimeric gene is linked to a chimeric gene for a bi-functional enzyme, AK-HDH, both activities of which are insensitive to feedback-inhibition by end-products of the biosynthetic pathway. Over-expression of feedback-insensitive AK-HDH directs the increased flux through the methionine-threonine branch of the aspartate-derived amino acid pathway, further increasing the potential for methionine and threonine biosynthesis.

A number of AK and AK-HDH genes have been isolated and sequenced. These include the thrA gene of *E. coli* [Katinka et al. (1980) Proc. Natl. Acad. Sci. USA 77:5730–5733], the metL gene of *E. coli* [Zakin et al. (1983) J. Biol. Chem. 258:3028–3031], the lysC gene of *E. coli* [Cassan et al. (1986) J. Biol. Chem. 20 261:1052–1057], and the HOM3 gene of *S. cerevisiae* [Rafalski et al. (1988) J. Biol. Chem. 263:2146–2151]. The thrA gene of *E. coli* encodes a bifunctional protein, AKI-HDHI. The AK activity of this enzyme is inhibited by threonine. The metL gene of *E. coli* also encodes a bifunctional protein, AKII-HDHII, and the AK activity of this enzyme is insensitive to all pathway end-products. The *E. coli* lysC gene encodes AKIII, which is sensitive to lysine inhibition. The HOM3 gene of yeast encodes an AK which is sensitive to threonine.

As indicated above AK genes are readily available to one skilled in the art for use in the present invention. A preferred class of AK genes encoding feedback-insensitive enzymes are derived from the *E. coli* lysC gene. Procedures useful for the isolation of the wild type *E. coli* lysC gene and lysine-insensitive mutations are presented in detail in Example 3.

The sequences of three mutant lysC genes that encode lysine-insensitive aspartokinase each differ from the wild type sequence by a single nucleotide, resulting in a single amino acid substitution in the protein. Other mutations could be generated at these target sites (see Example 3) in vitro by site-directed mutagenesis, using methods known to those skilled in the art. Such mutations would be expected to result in a lysine-insensitive enzyme. Furthermore, the in vivo method described in Example 3 could be used to easily isolate and characterize as many additional mutant lysC genes encoding lysine-insensitive AKIII as desired.

Another preferred class of AK genes are those encoding bi-functional enzymes, AK-HDH, wherein both catalytic activities are insensitive to end-product inhibition. A preferred AK-HDH enzyme is *E. coli* AKII-HDHII encoded by the metL gene. As indicated above, this gene has been isolated and sequenced previously. Thus, it can be easily obtained for use in the present invention by the same method used to obtain the lysC gene described in Example 3. Alternatively, the gene can be isolated from *E. coli* genomic DNA via PCR using oligonucleotide primers, which can be designed based on the published DNA sequence, as described in Example 7.

In addition to these genes, several plant genes encoding lysine-insensitive AK are known. In barley, lysine plus threonine-resistant mutants bearing mutations in two unlinked genes that result in two different lysine-insensitive AK isoenzymes have been described [Bright et al. (1982) Nature 299:278–279, Rognes et al. (1983) Planta 157:32–38, Arruda et al. (1984) Plant Phsiol. 76:442446]. In corn, a lysine plus threonine-resistant cell line had AK activity that was less sensitive to lysine inhibition than its parent line [Hibberd et al. (1980) Planta 148:183–187]. A subsequently isolated lysine plus threonine-resistant corn mutant is altered at a different genetic locus and also produces lysine-insensitive AK [Diedrick et al. (1990) Theor. Appl. Genet. 79:209–215, Dotson et al. (1990) Planta 182:546–552]. In tobacco there are two AK enzymes in leaves, one lysine-sensitive and one threonine-sensitive. A lysine plus threonine-resistant tobacco mutant that expressed completely lysine-insensitive AK has been described [Frankard et al. (1991) Theor. Appl. Genet. 82:273–282]. These plant mutants could serve as sources of genes encoding lysine-insensitive AK and used, based on the teachings herein, to increase the accumulation of methionine in the seeds of transformed plants.

A partial amino acid sequence of AK from carrot has been reported [Wilson et al. (1991) Plant Physiol. 97:1323:1328]. Using this information a set of degenerate DNA oligonucleotides could be designed, synthesized and used as hybridization probes to permit the isolation of the carrot AK gene. Recently the carrot AK gene has been isolated and its nucleotide sequence has been determined [Matthews et al. (1991) U.S. Ser. No. 07/746,705]. This gene was used as a heterologous hybridization probe to isolate the Arabidopsis thaliana AK-HDH gene [Ghislain et al. (1994) Plant Mol. Biol. 24:835–851], and thus can be used as a heterologous hybridization probe to isolate the plant genes encoding lysine-insensitive AK or AK-HDH described above.

Construction of Chimeric Genes for Expression of CS and AK in the Seeds of Plants In order to increase biosynthesis of methionine in seeds, suitable regulatory sequences are provided to create chimeric genes for high level seed-specific expression of the CS and AK or AK-HDH coding regions. The replacement of the native regulatory sequences accomplishes three things: 1) any methionine-concentration-dependent regulatory sequences are removed, permitting biosynthesis to continue in the presence of high levels of free methionine, 2) any pleiotropic effects that the accumulation of excess free methionine might have on the vegetative growth of plants is prevented because the chimeric gene(s) is not expressed in vegetative tissue of the transformed plants 3) high level expression of the enzyme(s) is obtained in the seeds.

The expression of foreign genes in plants is well-established [De Blaere et al. (1987) Meth. Enzymol.

143:277–291]. Proper level of expression of CS and AK or AK-HDH mRNAs may require the use of different chimeric genes utilizing different promoters. Such chimeric genes can be transferred into host plants either together in a single expression vector or sequentially using more than one vector. A preferred class of heterologous hosts for the expression of CS and AK or AK-HDH genes are eukaryotic hosts, particularly the cells of higher plants. Particularly preferred among the higher plants and the seeds derived from them are soybean, rapeseed (*Brassica napus, B. campestris*), sunflower (*Helianthus annus*), cotton (*Gossypium hirsutum*), corn, tobacco (*Nicotiana Tubacum*), alfalfa (*Medicago sativa*), wheat (*Triticum* sp), barley (*Hordeum vulgare*), oats (*Avena sativa, L*), sorghum (*Sorghum bicolor*), rice (*Oryza sativa*), and forage grasses. Expression in plants will use regulatory sequences functional in such plants.

The origin of the promoter chosen to drive the expression of the coding sequence is not critical as long as it has sufficient transcriptional activity to accomplish the invention by expressing translatable mRNA for CS and AK or AK-HDH genes in the desired host tissue.

Preferred promoters are those that allow expression of the protein specifically in seeds. This may be especially useful, since seeds are the primary source of vegetable amino acids and also since seed-specific expression will avoid any potential deleterious effect in non-seed organs. Examples of seed-specific promoters include, but are not limited to, the promoters of seed storage proteins. The seed storage proteins are strictly regulated, being expressed almost exclusively in seeds in a highly organ-specific and stage-specific manner [Higgins et al.(1984) Ann. Rev. Plant Physiol. 35:191–221; Goldberg et al. (1989) Cell 56:149–160; Thompson et al. (1989) BioEssays 10:108–113]. Moreover, different seed storage proteins may be expressed at different stages of seed development.

There are currently numerous examples for seed-specific expression of seed storage protein genes in transgenic dicotyledonous plants. These include genes from dicotyledonous plants for bean β-phaseolin [Sengupta-Goplalan et al. (1985) Proc. Natl. Acad. Sci. USA 82:3320–3324; Hoffman et al. (1988) Plant Mol. Biol. 11:717–729], bean lectin [Voelker et al. (1987) EMBO J. 6: 3571–3577], soybean lectin [Okamuro et al. (1986) Proc. Natl. Acad. Sci. USA 83:8240–8244], soybean kunitz trypsin inhibitor [Perez-Grau et al. (1989) Plant Cell 1:095–1109], soybean β-conglycinin [Beachy et al. (1985) EMBO J. 4:3047–3053; Barker et al. (1988) Proc. Natl. Acad. Sci. USA 85:458–462; Chen et al. (1988) EMBO J. 7:297–302; Chen et al. (1989) Dev. Genet. 10:112–122; Naito et al. (1988) Plant Mol. Biol. 11:109–123], pea vicilin [Higgins et al. (1988) Plant Mol. Biol. 11:683–695], pea convicilin [Newbigin et al. (1990) Planta 180:461], pea legumin [Shirsat et al. (1989) Mol. Gen. Genetics 215:326]; rapeseed napin [Radke et al. (1988) Theor. Appl. Genet. 75:685–694] as well as genes from monocotyledonous plants such as for maize 15 kD zein [Hoffman et al. (1987) EMBO J. 6:3213–3221; Schernthaner et al. (1988) EMBO J. 7:1249–1253; Williamson et al. (1988) Plant Physiol. 88:1002–1007], barley β-hordein [Marris et al. (1988) Plant Mol. Biol. 10:359–366] and wheat glutenin [Colot et al. (1987) EMBO J. 6:3559–3564]. Moreover, promoters of seed-specific genes, operably linked to heterologous coding sequences in chimeric gene constructs, also maintain their temporal and spatial expression pattern in transgenic plants. Such examples include linking either the Phaseolin or Arabidopsis 2S albumin promoters to the Brazil nut 2S albumin coding sequence and expressing such combinations in tobacco, Arabidopsis, or Brassica napus [Altenbach et al., (1989) Plant Mol. Biol. 13:513–522; Altenbach et al., (1992) Plant Mol. Biol. 18:235–245; De Clercq et al., (1990) Plant Physiol. 94:970–979], bean lectin and bean β-phaseolin promoters to express luciferase [Riggs et al. (1989) Plant Sci. 63:47–57], and wheat glutenin promoters to express chloramphenicol acetyl transferase [Colot et al. (1987) EMBO J. 6:3559–3564].

Of particular use in the expression of the nucleic acid fragment of the invention will be the heterologous promoters from several extensively-characterized soybean seed storage protein genes such as those for the Kunitz trypsin inhibitor [Jofuku et al. (1989) Plant Cell 1:1079–1093; Perez-Grau et al. (1989) Plant Cell 1:1095–1109], glycinin [Nielson et al. (1989) Plant Cell 1:313–328], β-conglycinin [Harada et al. (1989) Plant Cell 1:415425]. Promoters of genes for α'- and β-subunits of soybean β-conglycinin storage protein will be particularly useful in expressing the CS, AK and AK-HDH mRNAs in the cotyledons at mid- to late-stages of soybean seed development [Beachy et al. (1985) EMBO J. 4:3047–3053; Barker et al. (1988) Proc. Natl. Acad. Sci. USA 85:458–462; Chen et al. (1988) EMBO J. 7:297–302; Chen et al. (1989) Dev. Genet. 10:112–122; Naito et al. (1988) Plant Mol. Biol. 11:109–123] in transgenic plants, since: a) there is very little position effect on their expression in transgenic seeds, and b) the two promoters show different temporal regulation: the promoter for the α'-subunit gene is expressed a few days before that for the β-subunit gene.

Also of particular use in the expression of the nucleic acid fragments of the invention will be the promoters from several extensively characterized corn seed storage protein genes such as endosperm-specific promoters from the 10 kD zein [Kirihara et al. (1988) Gene 71:359–370], the 27 kD zein [Prat et al. (1987) Gene 52:51–49; Gallardo et al. (1988) Plant Sci. 54:211–281], and the 19 kD zein [Marks et al. (1985) J. Biol. Chem. 260:16451–16459]. The relative transcriptional activities of these promoters in corn have been reported [Kodrzyck et al. (1989) Plant Cell 1:105–114] providing a basis for choosing a promoter for use in chimeric gene constructs for corn. For expression in corn embryos, the strong embryo-specific promoter from the GLB1 gene [Kriz (1989) Biochemical Genetics 27:239–251, Wallace et al. (1991) Plant Physiol. 95:973–975] can be used.

It is envisioned that the introduction of enhancers or enhancer-like elements into other promoter constructs will also provide increased levels of primary transcription for CS and AK or AK-HDH genes to accomplish the invention. These would include viral enhancers such as that found in the 35S promoter [Odell et al. (1988) Plant Mol. Biol. 10:263–272], enhancers from the opine genes [Fromm et al. (1989) Plant Cell 1:977–984], or enhancers from any other source that result in increased transcription when placed into a promoter operably linked to the nucleic acid fragment of the invention.

Of particular importance is the DNA sequence element isolated from the gene for the α'-subunit of β-conglycinin that can confer 40-fold seed-specific enhancement to a constitutive promoter [Chen et al. (1988) EMBO J. 7:297–302; Chen et al. (1989) Dev. Genet. 10:112–122]. One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

Any 3' non-coding region capable of providing a polyadenylation signal and other regulatory sequences that may be required for the proper expression of the CS and AK coding regions can be used to accomplish the invention. This would include the 3' end from any storage protein such as the 3' end of the bean phaseolin gene, the 3' end of the soybean β-conglycinin gene, the 3' end from viral genes such as the 3' end of the 35S or the 19S cauliflower mosaic virus transcripts, the 3' end from the opine synthesis genes, the 3' ends of ribulose 1,5-bisphosphate carboxylase or chlorophyll a/b binding protein, or 3' end sequences from any source such that the sequence employed provides the necessary regulatory information within its nucleic acid sequence to result in the proper expression of the promoter/coding region combination to which it is operably linked. There are numerous examples in the art that teach the usefulness of different 3' non-coding regions [for example, see Ingelbrecht et al. (1989) Plant Cell 1:671–680].

DNA sequences coding for intracellular localization sequences may be added to the AK or AK-HDH coding sequence if required for the proper expression of the proteins to accomplish the invention. Plant amino acid biosynthetic enzymes are known to be localized in the chloroplasts and therefore are synthesized with a chloroplast targeting signal. The plant-derived CS coding sequence includes the native chloroplast targeting signal, but bacterial proteins such as *E. coli* AKIII and AKII-HDHII have no such signal. A chloroplast transit sequence could, therefore, be fused to the coding sequence. Preferred chloroplast transit sequences are those of the small subunit of ribulose 1,5-bisphosphate carboxylase, e.g. from soybean [Berry-Lowe et al. (1982) J. Mol. Appl. Genet. 1:483–498] for use in dicotyledonous plants and from corn [Lebrun et al. (1987) Nucleic Acids Res. 15:4360] for use in monocotyledonous plants.

Methionine-Rich Storage Protein Chimeric Genes

It may be useful for certain applications to incorporate the excess free methionine produced via deregulation of the biosynthetic pathway into a storage protein. This can help to prevent metabolism of the excess free methionine into such products as S-adenosyl-methionine, which may be undesirable. The storage protein chosen should contain higher levels of methionine than average proteins. Ideally, these methionine-rich storage proteins should contain at least 15% methionine by weight.

A number of methionine-rich plant seed storage proteins have been identified and their corresponding genes have been isolated. A gene in corn for a 15 kD zein protein containing about 15% methionine by weight [Pedersen et al. (1986) J. Biol. Chem. 261:6279–6284], a gene for a 10 kD zein protein containing about 30% methionine by weight [Kirihara et al. (1988) Mol. Gen. Genet. 21:477–484; Kirihara et al. (1988) Gene 71:359–370] have been isolated. A gene from Brazil nut for a seed 2S albumin containing about 24% methionine by weight has been isolated [Altenbach et al. (1987) Plant Mol. Biol. 8:239–250]. From rice a gene coding for a 10 kD seed prolamin containing about 25% methionine by weight has been isolated [Masumura et al. (1989) Plant Mol. Biol. 12:123–130]. A preferred gene, which encodes the most methionine-rich natural storage protein known, is an 18 kD zein protein designated high sulfur zein (HSZ) containing about 37% methionine by weight that has recently been isolated [PCT/US92/00958, see Example 4]. Thus, methionine-rich storage protein genes are readily available to one skilled in the art.

The above teachings on the construction of chimeric genes for high-level seed-specific expression of CS, AK and AK-HDH genes are also applicable to methionine-rich storage protein genes. Using these teachings, chimeric genes wherein regulatory sequences useful for obtaining high level seed-specific expression are linked to methionine-rich storage protein coding sequences are provided. In addition, there have been several reports on the expression of methionine-rich seed storage protein genes in transgenic plants. The high-methionine 2S albumin from Brazil nut has been expressed in the seeds of transformed tobacco under the control of the regulatory sequences from a bean phaseolin storage protein gene. The protein was efficiently processed from a 17 kD precursor to the 9 kD and 3 kD subunits of the mature native protein. The accumulation of the methionine-rich protein in the tobacco seeds resulted in an up to 30% increase in the level of methionine in the seeds [Altenbach et al. (1989) Plant Mol. Biol. 13:513–522]. This methionine-rich storage protein has also been efficiently expressed in Canola seeds [Altenbach et al. (1992) Plant Mol. Biol. 18:235–245.] In another case, high-level seed-specific expression of the 15 kD methionine-rich zein, under the control of the regulatory sequences from a bean phaseolin storage protein gene, was found in transformed tobacco; the signal sequence of the monocot precursor was also correctly processed in these transformed plants [Hoffman et al. (1987) EMBO J. 6:3213–3221]. As another example, the 18 kD zein protein containing 37% methionine has been expressed in tobacco and soybean seeds [PCT/US92/00958].

Introduction of Chimeric Genes into Plants

Various methods of introducing a DNA sequence into eukaryotic cells (i.e., of transformation) of higher plants are available to those skilled in the art (see EPO publications 0 295 959 A2 and 0 138 341 A1). Such methods include those based on transformation vectors utilizing the Ti and Ri plasmids of Agrobacterium spp. It is particularly preferred to use the binary type of these vectors. Ti-derived vectors transform a wide variety of higher plants, including monocotyledonous and dicotyledonous plants, such as soybean, cotton and rape [Pacciotti et al. (1985) Bio/Technology 3:241; Byrne et al. (1987) Plant Cell, Tissue and Organ Culture 8:3; Sukhapinda et al. (1987) Plant Mol. Biol. 8:209–216; Lorz et al. (1985) Mol. Gen. Genet. 199:178; Potrykus (1985) Mol. Gen. Genet. 199:183].

Other transformation methods are available to those skilled in the art, such as direct uptake of foreign DNA constructs [see EPO publication 0 295 959 A2], techniques of electroporation [see Fromm et al. (1986) Nature (London) 319:791] or high-velocity ballistic bombardment with metal particles coated with the nucleic acid constructs [see Kline et al. (1987) Nature (London) 327:70, and see U.S. Pat. No. 4,945,050]. Once transformed, the cells can be regenerated by those skilled in the art.

Of particular relevance are the recently described methods to transform foreign genes into commercially important crops, such as rapeseed [see De Block et al. (1989) Plant Physiol. 91:694–701], sunflower [Everett et al. (1987) Bio/Technology 5:1201], soybean [McCabe et al. (1988) Bio/Technology 6:923; Hinchee et al. (1988) Bio/Technology 6:915; Chee et al. (1989) Plant Physiol. 91:1212–1218; Christou et al. (1989) Proc. Natl. Acad. Sci USA 86:7500–7504; EPO Publication 0 301 749 A2], and corn [Gordon-Kamm et al. (1990) Plant Cell 2:603–618; Fromm et al. (1990) Biotechnology 8:833–839].

There are a number of methods that can be used to obtain plants containing multiple chimeric genes of this invention. Chimeric genes for seed-specifid expression of CS and AK or AD-HDH can be linked on a single nucleic acid fragment which can be used for transformation. Alternatively, a plant transformed with a CS chimeric gene can be crossed with a plant transformed with an AK or AK-HDH chimeric gene, and hybrid plants carrying both chimeric genes can be selected. In another method the CS and AK or AK-HDH chimeric genes, carried on separate DNA fragments, are co-transformed into the target plant and transgenic plants carrying both chimeric genes are selected. In yet another method a plant transformed with one of the chimeric genes is re-transformed with the other chimeric gene.

Similar methods can be used to obtain plants that contain a chimeric gene with a regulatory sequence capable of producing high level seed-specific expression for a methionine-rich storage protein gene along with a CS chimeric gene, with our without an AK or AK-HDH chimeric gene. Plants can be transformed with a nucleic acid fragment wherein a methionine-rich storage protein chimeric gene is linked to a CS chimeric gene, with or without an AK or AK-HDH chimeric gene. Alternatively, the CS, AK or AK-HDH, and methionine-rich storage protein chimeric genes can be co-transformed into the target plant and transgenic plant, or the methionine-rich storage protein gene can be introduced into previously transformed plants that contain a CS chimeric gene, with or without, an AK or AK-HDH chimeric gene. As another alternative, the methionine-rich storage protein gene can be introduced into a plant and the transformants obtained can be crossed with plants that contain a CS chimeric gene, with or without, an AK or AK-HDH chimeric gene.

Expression of Chimeric Genes in Transformed Plants

To analyze for expression of the chimeric CS, AK, AK-HDH and methionine-rich storage protein gene in seeds and for the consequences of expression on the amino acid content in the seeds, a seed meal can be prepared by any suitable method. The seed meal can be partially or completely defatted, via hexane extraction for example, if desired. Protein extracts can be prepared from the meal and analyzed for CS, AK or HDH enzyme activities. Alternatively the presence of any of the proteins can be tested for immunologically by methods well-known to those skilled in the art. To measure free amino acid composition of the seeds, free amino acids can be extracted from the meal and analyzed by methods known to those skilled in the art [Bieleski et al. (1966) Anal. Biochem. 17:278–293]. Amino acid composition can then be determined using any commercially available amino acid analyzer. To measure total amino acid composition of the seeds, meal containing both protein-bound and free amino acids can be acid hydrolyzed to release the protein-bound amino acids and the composition can then be determined using any commercially available amino acid analyzer. Seeds expressing the CS, AK, AK-HDH and/or methionine-rich storage proteins and with higher methionine content than the wild type seeds can thus be identified and propagated.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLE 1

Isolation of a Plant CS Gene

In order to clone the corn CS gene, RNA was isolated from developing seeds of corn line H99 19 days after pollination. This RNA was sent to Clontech Laboratories, Inc., (Palo Alto, Calif.) for the custom synthesis of a cDNA library in the vector Lambda Zap II. The conversion of the Lambda Zap II library into a phagemid library, then into a plasmid library was accomplished following the provided by Clontech. Once converted into a plasmid library the ampicilli-resistant clones obtained carry the cDNA insert in the vector pBluescript SK(-). Expression of the cDNA is under control of the lacZ promoter on the vector.

Two phagemid libraries were generated using the mixtures of the Lambda Zap II phage and the filamentous helper phage of 100 $\mu$L to 1 $\mu$L. Two additional libraries were generated using mixtures of 100 $\mu$L Lambda Zap II to 10 $\mu$L helper phage and 20 $\mu$L Lambda Zap II to 10 $\mu$L helper phage. The titers of the phagemid preparations were similar regardless of the mixture used and were about $2\times10^3$ ampicillin-resistant-transfectants per $\mu$L with $E.\ coli$ strain XL1-Blue as the host.

To identify clones that carried the CS gene, $E.\ coli$ strain BOB105 was constructed by introducing the F plasmid from $E.\ coli$ strain XL1-blue into strain UB 1005 [Clark (1984) FEMS Microbiol. Lett. 21:189] by conjugation. The genotype of BOB105 is: F'::Tn10 proA$^+$ B$^+$ lacI$^q$ $\Delta$(lacZ)M15/na1A37 metB1. The strain requires methionine for growth due to a mutation in the metB gene that encodes CS. Functional expression of the plant CS gene should complement the mutation and allow the strain to grow in the absence of methionine.

To select for clones from the corn cDNA library that carried the CS gene, 100 $\mu$L of the phagemid library was mixed with 300 $\mu$L of an overnight culture of BOB105 grown in L broth and incubated at 37° for 15 min. The cells were collected by centrifugation, resuspended in 400 $\mu$L of M9+vitamin B1 broth and plated on M9 media containing vitamin B1, glucose as a carbon and energy source, 20 $\mu$g/ml threonine (to prevent the possibility of threonine starvation due to overexpression of CS), 100 $\mu$g/mL ampicillin, 20 $\mu$g/mL tetracycline, and 0.16 mM IPTG (isopropylthio-$\beta$-galactoside). Fifteen plates were prepared and incubated at 37°. The amount of phagemid added was expected to yield about $2\times10^5$ ampicillin-resistant transfectants per plate.

Approximately 30 colonies (an average of 2 per plate or 1 per $10^5$ transfectants) able to grow in the absence of methionine were obtained. No colonies were observed if the phagemids carrying the corn cDNA library were not added. Twelve clones were picked and colony purified by streaking on the same medium described above. Plasmid DNA was isolated from the 12 clones and retransformed into BOB105. All of the 12 DNAs yielded methionine-independent transformants demonstrating that a plasmid-bome gene was responsible for the phenotype. Plasmid DNA was prepared from 7 of these clones and digested with restriction enzymes EcoR I and Xho I. Agarose gel electrophoresis of the digests revealed that 5 of the clones had EcoR I and Xho I sites at the ends of the inserts, as expected from the method used to create the cDNA library. Three of five plasmids analyzed had a common internal Taq I fragment, indicating that these plasmids were related. One of three related DNA inserts, derived from plasmid pFS1088, as well as another unrelated DNA insert, from plasmid pFS 1086, was completely sequenced.

The DNA insert in plasmid pFS1086 is 1048 bp in length and contains a long open reading frame and a poly A tail, indicating that it represents a corn cDNA. The deduced amino acid sequence of the open reading frame shows no similarity to the published sequence of E. coli CS [Duchange et al. (1983) J. Biol. Chem. 258:14868–14871]. None of the proteins in the GenBank database showed significant amino acid sequence similarity to the pFS1086 reading frame. Thus, the function of the protein encoded on plasmid pFS 1086 and the reason for its ability to complement the metB mutation in BOB105 is unknown.

The sequence of the DNA insert in plasmid pFS1088 is shown in SEQ ID NO:1. It is 1639 bp in length and contains a long open reading frame and a poly A tail, indicating that it too represents a corn cDNA. The deduced amino acid sequence of the open reading frame shows 59 percent similarity and 34 percent identity to the published sequence of E. coli CS (see FIG. 1), indicating that it represents a corn homolog to the E. coli metB gene. Comparison of the amino acid sequences reveals that amino acid 89 of corn CS aligns with amino acid 1 of the E. coli protein. Since most amino acid biosynthetic enzymes are localized in chloroplasts, it is likely that the first 88 amino acids of corn CS is a chloroplast targeting signal, which is absent in the bacterial protein. The amino acid sequence in this region has many of the features characteristic of chloroplast targeting signals, namely a deficiency in negatively charged amino acids and a net positive charge, a large percentage of the hydroxylated amino acids serine and threonine (22%), and a large percentage of the small hydrophobic amino acids alanine and valine (22%).

The open reading frame in plasmid pFS1088 continues to the 5' end of the insert DNA, and does not include an ATG initiator codon, indicating that the cloned cDNA is incomplete. Since chloroplast targeting signals range from about 30 to 100 amino acids in length, and 88 amino acids are present upstream of the homology between the E. coli and corn CS, it is likely that most of the coding sequence, including a functional chloroplast targeting signal, is contained in the cloned insert. The open reading frame of pFS1088 is in frame with the initiator codon of the lacZ gene carried on the cloning vector. Thus, complementation of the metB mutation in BOB105 results from expression of a fusion protein including 37 amino acids from β-galactosidase and the vector polylinker attached to the truncated corn CS protein.

In order to clone the entire 5' end of the corn CS gene the cDNA clone was used as a DNA hybridization probe to screen a genomic corn library. A genomic library of corn in bacteriophage lambda was purchased from Stratagene (La Jolla, Calif.). Data sheets from the supplier indicated that the corn DNA was from etiolated Missouri 17 corn seedlings. The vector was Lambda FIX™ II carrying Xho I fragments 9–23 kb in size. A titer of $1.0 \times 10^{10}$ plaque forming units (pfu)/mL in the amplified stock was indicated by the supplier when purchased. Prior to screening, the library was re-titered and contained $2.0 \times 10^8$ pfu/mL.

The protocol for screening the library by DNA hybridization was provided by Clonetech (Palo Alto, Calif.). About 30,000 pfu were plated per 150-mm plate on a total of 12 NZCYM agarose plates giving 360,000 plaques. Plating was done using E. coli LE392 grown in LB+0.2% maltose+10 mM $MgSO_4$ as the host and NZCYM-0.7% agarose as the plating medium. The plaques were grown overnight at 37° C. and placed at 4° C. for one hour prior to lifting onto filters. The plaques were absorbed onto nylon membranes (Amersham Hybond-N, 0.45 mM pore size), two lifts from each plate, denatured in 0.5M NaOH, 1.5M NaCl, neutralized in 1.5M NaCl, 1.0M Tris-Cl pH 8.0, and rinsed in 2×SSC [Sambrook et al. (1989) Molecular Cloning: A Laboratory Manual, Cold Spring Harbor Laboratory Press; Boehringer Mannheim Biochemicals, The Genius™ System User's Guide for Filter Hybridization, Version 2.0]. The filters were blotted on Whatman 3MM paper and heated in a vacuum oven at 80° C. for two hours.

A digoxigenin-11-dUTP labeled corn cDNA CS probe was prepared by random primed DNA labeling using Genius 2 DNA Labeling Kit (Boehringer Mannheim Biochemicals, The Genius™ System User's Guide for Filter Hybridization, Version 2.0). The DNA fragment used for labeling was an Nco I to BspH I (1390 bp) from plasmid pFS1088 isolated by low melting point (LMP) agarose gel electrophoresis and NACS purification (Bethesda Research Laboratories). The 1390 bp band was excised from 0.7% LMP agarose, melted, and diluted into 0.5M NaCl and loaded onto a NACS column, which was then washed with 0.5M NaCl, 10 mM Tris-Cl, pH 7.2, 1 mM EDTA and the fragment eluted with 2M NaCl, 10 mM Tris-Cl, pH 7.2, 1 mM EDTA. An estimate of the yield of DIG-labeled DNA followed the Boehringer Mannheim Biochemicals procedure for chemiluminescent detection with Lumi-Phos 530 replacing the 2% Blocking reagent for nucleic acid hybridization with 5% Blotting Grade Blocker (Bio-Rad Laboratories, Hercules, Calif.).

The twenty-four 150-mm nylon filters carrying the λ phage plaques were prewashed in 0.1× SSC, 0.5% SDS at 65° C. for one hour. Overnight prehybridization at 65° C. was carried out in 5× SSC [see Sambrook et al. (1989) Molecular Cloning: A Laboratory Manual, Cold Spring Harbor Laboratory Press], 0.5% Blocking reagent for nucleic acid hybridization (Boehringer Mannheim Biochemicals), 1.0% N-lauroylsarcosine, and 0.2% SDS. The filters were hybridized overnight in fresh prehybridization solution with denatured DIG-labeled corn CS cDNA probe at 10 ng DIG-labeled DNA/ml of hybridization solution at 65° C. They were rinsed the following day under stringent conditions: two times for 5 minutes at room temp in 2× SSC—0.01% SDS and two times 30 minutes at 65° C. in 0.1× SSC—0.1% SDS. Filters were then processed following the Boehringer Mannheim Biochemicals procedure for chemiluminescent detection with Lumi-Phos 530 with modifications as described above. From the autoradiograms of the duplicate filters, 11 hybridizing plaques were identified. These plaques were picked from the original petri plate and plated out at a dilution to yield about 1000 plaques per 80-mm plate. These plaques were absorbed to nylon filters and re-probed using the same procedure. After autoradiography, two of the original plaques, number 6-1 and number 10-1, showed hybridizing plaques. These plaques were tested with the probe a third time; and well isolated plaques were picked from each original. Following a fourth probing all the plaques hybridized, indicating that pure clones had been isolated.

DNA was prepared from these two phage clones, λ6-1 and λ10-1, using the protocol for plate lysate method [see Sambrook et al. (1989) Molecular Cloning: A Laboratory Manual, Cold Spring Harbor Laboratory Press]. Restriction endonuclease digests and agarose gel electrophoresis showed the two clones to be identical. The DNA fragments from the agarose gel were "Southern-blotted" [see Sambrook et al. (1989) Molecular Cloning: A Laboratory Manual, Cold Spring Harbor Laboratory Press] onto nylon filters and probed with DIG-labeled corn CS cDNA as described above. A single 7.5 kb Sal I fragment and two Xba I fragments of 3.6 kb and 3.2 kb hybridized to the probe. The 3.2 kb Xba I fragment hybridized weakly to the probe whereas the 3.6 kb Xba I and the 7.5 kb Sal I fragments hybridized strongly.

The 7.5 kb Sal I fragment and the 3.6 kb and 3.2 kb Xba I fragments were isolated from digests of the λ DNA run on an 0.7% low melting point (LMP) agarose gel. The 7.5 kb, 3.6 kb and 3.2 kb bands were excised, melted, and diluted into 0.5M NaCl and loaded onto NACS columns, which were then washed with 0.5M NaCl, 10 mM Tris-Cl, pH 7.2, 1 mM EDTA and the fragment eluted with 2M NaCl, 10 mM Tris-Cl, pH 7.2, 1 mM EDTA. The 7.5 kb fragment was ligated to the phagemid pGEM®-9Zf(-) (Promega, Madison, Wis.) which had been cleaved with Sal I and treated with calf intestinal alkaline phosphatase [see Sambrook et al. (1989) Molecular Cloning: A Laboratory Manual, Cold Spring Harbor Laboratory Press] to prevent ligation of the phagemid to itself. Subclones with this fragment in both orientations with respect to the pGEM®-9Zf(-) DNA were obtained following transformation of *E. coli*. The 3.6 kb and 3.2 kb Xba I fragments were similarly cloned into the Xba I site of pGEM®-9Zf(-) that had been treated with calf intestimal alkaline phosphatase. Two subclones from each Xba I fragment with the fragments in both orientations with respect to pGEM®-9Zf(-) DNA were obtained following transformation of *E. coli*. The two 3.6 kb Xba I subclones were designated pFS1179 and pFS1180.

Restriction enzyme analysis of the subclones suggested that the 3.6 kb Xba I fragment in pFS1179 and pFS1180 included the 5' region of the corn CS gene. Preliminary sequence analysis of these clones using primers internal to the 5' end of the cDNA confirmed that the clones contained the 5' end of the genomic CS gene. The combined sequence and restriction enzyme analysis suggested that the 3.6 kb Xba I fragment contained the entire 5' region encoding the chloroplast targeting signal as well as an additional approximately 800 bp of sequence in the promoter region of the gene.

DNA from pFS1180 was sent to LARK Sequencing Technologies Inc. (Houston, Tex.) for complete DNA sequencing analysis. The 3.6 kb Xba I fragment was blunt-ended, cloned into the EcoR V site of pBluescript II SK⁺ (Stratagene, LaJolla, Calif.) and transformed into *E. coli*. Nested deletions were generated from both the T7 and T3 ends using Exo III and S1 nuclease. Plasmid DNA was prepared using a modified alkaline lysis procedure. Deletion clones were size-selected for DNA sequencing by electrophoresis on agarose gels. DNA sequencing was performed using standard dideoxynucleotide termination reactions containing 7-deaza dGTP. 7-deaza dITP was used, if necessary, to resolve severe GC band compressions. The label was [$^{35}$S]dATP. Sequencing reactions were analysed on 6% polyacrylamide wedge gels containing 8M urea. The entire 3639 bp Xba I fragment was sequenced (see SEQ ID NO:26).

Complete sequence analysis of the 3639 bp Xba I fragment revealed it includes 806 bp of sequence upstream from the protein coding region and 2833 bp of DNA encoding two-thirds of the corn CS protein. The 2833 bp includes seven exons and seven introns with the 3' Xba I site located in the seventh intron. Table 1 describes the location and length of exons and introns in the sequence as well the number of amino acids encoded by the exons. The first exon includes the entire chloroplast targeting signal and 12 amino acids into the region that shows amino acid sequence alignment with the *E. coli* protein (FIG. 1). The last codon in Exon 7 encodes amino acid 333 of corn CS as shown in SEQ ID NO:1.

TABLE 1

| REGION | FROM bp | TO bp | LENGTH in bp | # AMINO ACIDS ENCODED |
| --- | --- | --- | --- | --- |
| Promoter | 1 | 806 | 806 | na |
| Exon1 | 807 | 1194 | 387 | 129 |
| Intron1 | 1195 | 1301 | 106 | na |
| Exon2 | 1302 | 1405 | 103 | 35 |
| Intron2 | 1406 | 1489 | 83 | na |
| Exon3 | 1490 | 1563 | 73 | 24 |
| Intron3 | 1564 | 1646 | 82 | na |
| Exon4 | 1647 | 1815 | 168 | 57 |
| Intron4 | 1816 | 2507 | 691 | na |
| Exon5 | 2508 | 2567 | 59 | 20 |
| Intron5 | 2568 | 2660 | 92 | na |
| Exon6 | 2661 | 2864 | 203 | 68 |
| Intron6 | 2865 | 2947 | 82 | na |
| Exon7 | 2948 | 3034 | 86 | 29 |
| Intron7 | 3035 | 3639 | >604 | na |

Comparison of the corn CS cDNA sequence to the genomic CS DNA sequence indicated that the cDNA of clone pFS1088 did not contain the entire chloroplast targeting signal as anticipated. The cDNA was not truncated on the 5' end, but contained a 170 bp deletion in the chloroplast transit sequence (FIG. 2). Southern blot analysis of genomic DNA from corn lines H99 and Missouri 17 confirmed that the sequence difference was due to a deletion in the cDNA. This deletion placed the correct CS ATG initiator codon, which is located at nucleotides 85–87 of SEQ ID NO:1, out of frane with the initiator codon of the lacZ gene carried on the cloning vector. The cDNA sequence returned to the proper CS coding frame at amino acid 62 near the 3' end of the deleted sequence. Complementation of the metB mutation in BOB105 resulted from expression of a fusion protein including 37 amino acids from β-galactosidase and the vector polylinker plus 61 amino acids that are encoded by the corn CS sequence, but are from the incorrect reading frame, for a total of 98 amino acids attached to the amino terminus of the corn CS protein. Thus, the corn CS protein can tolerate extra amino acids fused to its amino terminus without loss of function.

Comparison of the corn CS cDNA sequence 3' to the deletion region with the genomic sequence (with introns removed) shows 96 percent identity. Comparison of the two DNA sequences 5' to the deletion region shows 88% identity. The deduced amino acid sequence of the open reading frame of the cDNA 3' to the deleted sequence shows 99.3% similarity and 98.9% identity when compared to the deduced amino acid sequence from the exons of the genomic CS sequence. When the correct reading frame is translated from the cDNA 5' to the deleted sequence the deduced amino acid sequence shows 100% identity to the deduced amino acid sequence translated from the exons of the genomic CS sequence in this region. The complete amino acid sequence of the corn CS protein derived from combining the amino terminal sequence deduced from the corn genomic DNA fragment of SEQ ID NO:26 and the carboxy terminal sequence from the corn cDNA fragment of SEQ ID NO:1 is shown in SEQ ID NO:27.

EXAMPLE 2

Modification of the Corn CS Gene and High Level Expression in *E. coli*

As indicated in Example 1, the open reading frame in plasmid pFS1088 for the corn CS gene does not include an ATG initiator codon. Oligonucleotide adaptors OTG145 and OTG146 were designed to add an initiator codon in frame with the CS coding sequence.

OTG145=SEQ ID NO:2: AATTCATGAG TGCA

OTG146=SEQ ID NO:3: AATTTGCACT CATG

When annealed the oligonucleotides possess EcoR I sticky ends. Upon insertion into pFS1088 in the desired orientation, an EcoR I site is present at the 5' end of the adaptor, the ATG initiator codon is within a BspH I restriction endonuclease site, and the EcoR I site at the 3' end of the adaptor is destroyed. The oligonucleotides were ligated into EcoR I digested pFS1088, and insertion of the correct sequence in the desired orientation was verified by DNA sequencing.

To achieve high level expression of the corn CS gene in E. coli the bacterial expression vector pBT430 was used. This expression vector is a derivative of pET-3a [Rosenberg et al. (1987) Gene 56:125–135] which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

The corn CS gene was cut out of the modified pFS1088 plasmid described above as an 1482 bp BspH I fragment and inserted into the expression vector pBT430 digested with Nco I. Clones with the CS gene in the proper orientation were identified by restriction enzyme mapping.

For high level expression each of the plasmids was transformed into E. coli strain BL21(DE3) or BL21(DE3) lysS [Studier et al. (1986) J. Mol. Biol. 189:113–130]. Cultures were grown in LB medium containing ampicillin (100 mg/L) at 37° C. At an optical density at 600 nm of approximately 1, IPTG (isopropylthio-β-galactoside, the inducer) was added to a final concentration of 0.4 mM and incubation was continued overnight. The cells were collected by centrifugation and resuspended in 1/20th the original culture volume in 50 mM NaCl; 50 mM Tris-Cl, pH 7.5; 1 mM EDTA, and frozen at −20° C. Frozen aliquots of 1 mL were thawed at 37° C. and sonicated, in an ice-water bath, to lyse the cells. The lysate was centrifuged at 4° C. for 5 min at 12,000 rpm. The supernatant was removed and the pellet was resuspended in 1 mL of the above buffer.

The supernatant and pellet fractions of uninduced and IPTG-induced cultures were analyzed by SDS polyacrylamide gel electrophoresis. The best of the conditions tested was the induced culture of the BL21(DE3)lysS host. The major protein visible by Coomassie blue staining in the pellet fraction of this induced culture had a molecular weight of about 54 kd, the expected size for corn CS.

EXAMPLE 3

Isolation of the E. coli lysC Gene and Mutations in lysC Resulting in Lysine-insensitive AKIII The E. coli lysC gene has been cloned, restriction endonuclease mapped and sequenced previously [Cassan et al. (1986) J. Biol. Chem. 261:1052–1057]. For the present invention the lysC gene was obtained on a bacteriophage lambda clone from an ordered library of 3400 overlapping segments of cloned E. coli DNA constructed by Kohara, Akiyama and Isono [Kohara et al. (1987) Cell 50:595–508]. This library provides a physical map of the whole E. coli chromosome and ties the physical map to the genetic map. From the knowledge of the map position of lysC at 90 min. on the E. coli genetic map [Theze et al. (1974) J. Bacteriol. 117:133–143], the restriction endonuclease map of the cloned gene [Cassan et al. (1986) J. Biol. Chem. 261:1052–1057], and the restriction endonuclease map of the cloned DNA fragments in the E. coli library [Kohara et al. (1987) Cell 50:595–508], it was possible to choose lambda phages 4E5 and 7A4 [Kohara et al. (1987) Cell 50:595–508] as likely candidates for carrying the lysC gene. The phages were grown in liquid culture from single plaques as described [see Current Protocols in Molecular Biology (1987) Ausubel et al. eds. John Wiley & Sons New York] using LE392 as host [see Sambrook et al. (1989) Molecular Cloning: a Laboratory Manual, Cold Spring Harbor Laboratory Press]. Phage DNA was prepared by phenol extraction as described [see Current Protocols in Molecular Biology (1987) Ausubel et al. eds. John Wiley & Sons New York].

From the sequence of the gene several restriction endonuclease fragments diagnostic for the lysC gene were predicted, including an 1860 bp EcoR I-Nhe I fragment, a 2140 bp EcoR I-Xmn I fragment and a 1600 bp EcoR I-BamH I fragment. Each of these fragments was detected in both of the phage DNAs confirming that these carried the lysC gene. The EcoR I-Nhe I fragment was isolated and subcloned in plasmid pBR322 digested with the same enzymes, yielding an ampicillin-resistant, tetracycline-sensitive E. coli transformant. The plasmid was designated pBT436.

To establish that the cloned lysC gene was functional, pBT436 was transformed into E. coli strain Gif106M1 (E. coli Genetic Stock Center strain CGSC-5074) which has mutations in each of the three E. coli AK genes [Theze et al. (1974) J. Bacteriol. 117:133–143]. This strain lacks all AK activity and therefore requires diaminopimelate (a precursor to lysine which is also essential for cell wall biosynthesis), threonine and methionine. In the transformed strain all these nutritional requirements were relieved demonstrating that the cloned lysC gene encoded functional AKIII.

Addition of lysine (or diaminopimelate which is readily converted to lysine in vivo) at a concentration of approximately 0.2 mM to the growth medium inhibits the growth of Gif106M1 transformed with pBT436.M9 media [see Sambrook et al. (1989) Molecular Cloning: a Laboratory Manual, Cold Spring Harbor Laboratory Press] supplemented with the arginine and isoleucine, required for Gif106M1 growth, and ampicillin, to maintain selection for the pBT436 plasmid, was used. This inhibition is reversed by addition of threonine plus methionine to the growth media. These results indicated that AKIII could be inhibited by exogenously added lysine leading to starvation for the other amino acids derived from aspartate. This property of pBT436-transformed Gif106M1 was used to select for mutations in lysC that encoded lysine-insensitive AKIII.

Single colonies of Gif106M1 transformed with pBT436 were picked and resuspended in 200 μL of a mixture of 100 μL 1% lysine plus 100 μL of M9 media. The entire cell suspension containing $10^7$–$10^8$ cells was spread on a petri dish containing M9 media supplemented with the arginine, isoleucine, and ampicillin. Sixteen petri dishes were thus prepared. From 1 to 20 colonies appeared on 11 of the 16 petri dishes. One or two (if available) colonies were picked and retested for lysine resistance and from this nine lysine-resistant clones were obtained. Plasmid DNA was prepared from eight of these and re-transformed into Gif106M1 to determine whether the lysine resistance determinant was plasmid-borne. Six of the eight plasmid DNAs yielded lysine-resistant colonies. Three of these six carried lysC genes encoding AKIII that was uninhibited by 15 mM lysine, whereas wild type AKIII is 50% inhibited by 0.3–0.4 mM lysine and >90% inhibited by 1 mM lysine (see Example 2 for details).

To determine the molecular basis for lysine-resistance the sequences of the wild type lysC gene and three mutant genes were determined. The sequence of the wild Wpe lysC gene cloned in pBT436 (SEQ ID NO:4) differed from the published lysC sequence in the coding region at 5 positions. Four of these nucleotide differences were at the third position in a codon and would not result in a change in the amino acid sequence of the AKIII protein. One of the differences would result in a cysteine to glycine substitution at amino acid 58 of AKIII. These differences are probably due to the different strains from which the lysC genes were cloned.

The sequences of the three mutant lysC genes that encoded lysine-insensitive AK each differed from the wild type sequence by a single nucleotide, resulting in a single amino acid substitution in the protein. Mutant M2 had an A substituted for a G at nucleotide 954 of SEQ ID NO:4 resulting in an isoleucine for methionine substitution at amino acid 318 and mutants M3 and M4 had identical T for C substitutions at nucleotide 1055 of SEQ ID NO:4 resulting in an isoleucine for threonine substitution at amino acid 352. Thus, either of these single amino acid substitutions is sufficient to render the AKIII enzyme insensitive to lysine inhibition.

An Nco I (CCATGG) site was inserted at the translation initiation codon of the lysC gene using the following oligonucleotides:

SEQ ID NO:5: GATCCATGGC TGAAATTGTT GTCTCCAAAT TTGGCG

SEQ ID NO:6: GTACCGCCAA ATTTGGAGAC AACAATTTCA GCCATG

When annealed these oligonucleotides have BamH I and Asp 718 "sticky" ends. The plasmid pBT436 was digested with BamH I, which cuts upstream of the lysC coding sequence and Asp 718 which cuts 31 nucleotides downstream of the initiation codon. The annealed oligonucleotides were ligated to the plasmid vector and E. coli transformants were obtained. Plasmid DNA was prepared and screened for insertion of the oligonucleotides based on the presence of an Nco I site. A plasmid containing the site was sequenced to assure that the insertion was correct, and was designated pBT457. In addition to creating an Nco I site at the initiation codon of lysC, this oligonucleotide insertion changed the second codon from TCT, coding for serine, to GCT, coding for alanine. This amino acid substitution has no apparent effect on the AKIII enzyme activity.

The lysC gene was cut out of plasmid pBT457 as a 1560 bp Nco I-EcoR I fragment and inserted into the expression vector pBT430 digested with the same enzymes, yielding plasmid pBT461. For expression of the mutant lysC-M4 gene pBT461 was digested with Kpn I-EcoR I, which removes the wild type lysC gene from about 30 nucleotides downstream from the translation start codon, and inserting the analogous Kpn I-EcoR I fragments from the mutant genes yielding plasmid pBT492.

EXAMPLE 4

Molecular Cloning of Corn Genes Encoding Methionine-Rich Seed Storage Proteins

A high methionine 10 kD zein gene [Kirihara et al. (1988) Mol. Gen. Genet. 211:477–484] was isolated from corn genomic DNA using PCR. Two oligonucleotides 30 bases long flanking this gene were synthesized using an Applied Biosystems DNA synthesizer. Oligomer SM56 (SEQ ID NO:7) codes for the positive strand spanning the first ten amino acids:

SM56 5'-ATGGCAGCCA AGATGCTTGC ATTGTTCGCT-3'  (SEQ ID NO:7)

Oligomer CFC77 (SEQ ID NO:8) codes for the negative strand spanning the last ten amino acids:

CFC77 5'-GAATGCAGCA CCAACAAAGG GTTGCTGTAA-3'  (SEQ ID NO:8)

These were employed to generate by polymerase chain reaction (PCR) the 10 kD coding region using maize genomic DNA from strain B85 as the template. PCR was performed using a Perkin-Elmer Cetus kit according to the instructions of the vendor on a thermocycler manufactured by the same company. The reaction product when run on a 1% agarose gel and stained with ethidium bromide showed a strong DNA band of the size expected for the 10 kD zein gene, 450 bp, with a faint band at about 650 bp. The 450 bp band was electro-eluted onto DEAE cellulose membrane (Schleicher & Schuell) and subsequently eluted from the membrane at 65° C. with 1M NaCl, 0.1 mM EDTA, 20 mM Tris-Cl, pH 8.0. The DNA was ethanol precipitated and rinsed with 70% ethanol and dried. The dried pellet was resuspended in 10 $\mu$L water and an aliquot (usually 1 $\mu$L) was used for another set of PCR reactions, to generate by asymmetric priming single-stranded linear DNAs. For this, the primers SM56 and CFC77 were present in a 1:20 molar ratio and 20:1 molar ratio. The products, both positive and negative strands of the 10 kD zein gene, were phenol extracted, ethanol precipitated, and passed through NACS (Bethesda Research Laboratories) columns to remove the excess oligomers. The eluates were ethanol precipitated twice, rinsed with 70% ethanol, and dried. DNA sequencing was done using the appropriate complementary primers and a sequenase kit from United States Biochemicals Company according to the vendors instructions. The sequence deviated from the published coding sequence (Kirihara et al., Gene, 71:359–370 (1988)) in one base pair at nucleotide position 1504 of the published sequence. An A was changed to a G which resulted in the change of amino acid 123 (with the initiator methionine as amino acid 1) from Gln to Arg. It is not known if the detected mutation was generated during the PCR reaction or if this is another allele of the maize 10 kD zein gene. A radioactive probe was made by nick-translation of the PCR-generated 10 kD zein gene using $^{32}$P-dCrP and a nick-translation kit purchased from Bethesda Research Laboratories.

A genomic library of corn in bacteriophage lambda was purchased from Clontech (Palo Alto, Calif.). Data sheets from the supplier indicated that the corn DNA was from seven-day-old seedlings grown in the dark. The vector was $\lambda$-EMBL-3 carrying BamHI fragments 15 kb in average size. A titer of 1 to 9×10$^9$ plaque forming units (pfu)/mL was indicated by the supplier. Upon its arrival the library was titered and contained 2.5×10$^9$ pfu/mL.

The protocol for screening the library by DNA hybridization was provided by the vendor. About 30,000 pfu were plated per 150-mm plate on a total of 15 Luria Broth (LB) agar plates giving 450,000 plaques. Plating was done using E. coli LE392 grown in LB+0.2% maltose as the host and LB–0.7% agarose as the plating medium. The plaques were absorbed onto nitrocellulose filters (Millipore HATF, 0.45 mM pore size), denatured in 0.5M NaOH, neutralized in 1.5M NaCl, 0.5M Tris-Cl pH 7.5, and rinsed in 3×SSC [Sambrook et al. (1989) Molecular Cloning: A Laboratory Manual, Cold Spring Harbor Laboratory Press]. The filters were blotted on Whatman 3MM paper and heated in a vacuum oven at 80° C. for two hours to allow firm anchorage of phage DNA in the membranes.

The $^{32}$P-labelled 10 kD DNA fragment zein was used as a hybridization probe to screen the library. The fifteen 150-mm nitrocellulose filters carrying the λ phage plaques were screened using radioactive 10 kD gene probe. After four hours prehybridizing at 60° C. in 50×SSPE, 5× Denhardt's, [see Sambrook et al. (1989) Molecular Cloning: A Laboratory Manual, Cold Spring Harbor Laboratory Press] 0.1% SDS, 100 μg/mL calf thymus DNA, the filters were transferred to fresh hybridization mix containing the denatured radiolabeled 10 kD zein gene (cpm/mL) and stored overnight at 60° C. They were rinsed the following day under stringent conditions: one hour at room temp in 2×SSC—0.05% SDS and one hour at 68° C. in 1×SSC—0.1% SDS. Blotting on 3MM Whatman paper followed, then air drying and autoradiography at −70° C. with Kodak XAR-5 films with DuPont Cronex® Lightning Plus intensifying screens. From these autoradiograms, 20 hybridizing plaques were identified. These plaques were picked from the original petri plate and plated out at a dilution to yield about 100 plaques per 80-mm plate. These plaques were absorbed to nitrocellulose filters and re-probed using the same procedure. After autoradiography only one of the original plaques, number 10, showed two hybridizing plaques. These plaques were tested with the probe a third time; all the progeny plaques hybridized, indicating that pure clones had been isolated.

DNA was prepared from these two phage clones, λ10-1, λ10-2, using the protocol for DNA isolation from small-scale liquid λ-phage lysates (Ansul et al. (1987) Current Protocols in Molecular Biology, pp. 1.12.2, 1.13.5–6). Restriction endonuclease digests and agarose gel electrophoresis showed the two clones to be identical. The DNA fragments from the agarose gel were "Southern-blotted" [see Sambrook et al. (1989) Molecular Cloning: A Laboratory Manual, Cold Spring Harbor Laboratory Press] onto nitrocellulose membrane filters and probed with radioactively-labeled 10 kD zein DNA generated by nick translation. A single 7.5 kb BamH I fragment and a single 1.4 kb Xba I fragment hybridized to the probe.

The 7.5 kb BamH I fragment was isolated from a BamH I digest of the λ DNA run on an 0.5% low melting point (LMP) agarose gel. The 7.5 kb band was excised, melted, and diluted into 0.5M NaCl and loaded onto a NACS column, which was then washed with 0.5M NaCl, 10 mM Tris-Cl, pH 7.2, 1 mM EDTA and the fragment eluted with 2M NaCl, 10 mM Tris-Cl, pH 7.2, 1 mM EDTA. This fragment was ligated to the phagemid pTZ18R (Pharmacia) which had been cleaved with BamH I and treated with calf intestinal alkaline phosphatase [see Sambrook et al. (1989) Molecular Cloning: A Laboratory Manual, Cold Spring Harbor Laboratory Press] to prevent ligation of the phagemid to itself. Subclones with these fragments in both orientations with respect to the pTZ18R DNA were obtained following transformation of E. coli.

An Xba I digest of the cloned λ phage DNA was run on an 0.8% agarose gel and a 1.4 kb fragment was isolated using DEAE cellulose membrane (same procedure as for the PCR-generated 10 kD zein DNA fragment described above). This fragment was ligated to pTZ18R cut with Xba I in the same way as described above. Subclones with these fragments in both orientations with respect to the pTZ18R DNA, designated pX8 and pX10, were obtained following transformation of E. coli. Single-stranded DNAs were made from the subclones using the protocol provided by Pharmacia. The entire 1.4 kb Xba I fragments were sequenced. An additional 700 bases adjacent to the Xba I fragment was sequenced from the BamH I fragment in clone pB3 (fragment pB3 is in the same orientation as pX8) giving a total of 2123 bases of sequence (SEQ ID NO:9).

Encoded on this fragment is another methionine-rich zein, which is related to the 10 kD zein and has been designated High Sulfur Zein (HSZ) [see PCT/US 92/00958]. From the deduced amino acid sequence of the protein, its molecular weight is approximately 21 kD and it is about 38% methionine by weight.

EXAMPLE 5

Modification of the HSZ Gene by Site-Directed Mutagenesis

Three Nco I sites were present in the 1.4 kD Xba I fragment carrying the HSZ gene, all in the HSZ coding region. It was desirable to maintain only one of these sites (nucleotides 751–756 in SEQ ID NO:9) that included the translation start codon. Therefore, the Nco I sites at positions 870–875 and 1333–1338 were eliminated by oligonucleotide-directed site-specific mutagenesis [see Sambrook et al. (1989) Molecular Cloning: A Laboratory Manual, Cold Spring Harbor Laboratory Press]. The oligonucleotides synthesized for the mutagenesis were:

CFC99 ATGAACCCTT GGATGCA (SEQ ID NO:10)

CFC98 CCCACAGCAA TGGCGAT (SEQ ID NO:11)

Mutagenesis was carried out using a kit purchased from Bio-Rad (Richmond, Calif.), following the protocol provided by the vendor.

The process changed the A to T at 872 and the C to A at 1334. These were both at the third position of their respective codons and resulted in no change in the amino acid sequence encoded by the gene, with C C A to C C T, still coding for Pro and G C C to G C A, still coding for Ala. The plasmid clone containing the modified HSZ gene with a single Nco I site at the ATG start codon was designated pX8m. Because the native HSZ gene has a unique Xba I site at the stop codon of the gene (1384–1389, SEQ ID NO:9), a complete digest of the DNA with Nco I and Xba I yields a 637 bp fragment containing the entire coding sequence of the precursor HSZ polypeptide (SEQ ID NO:12).

It was desirable to create a form of the HSZ gene with alternative unique restriction endonuclease sites just past the end of the coding region. To do this oligonucleotides CFC104 (SEQ ID NO:13) and CFC105 (SEQ ID NO:14):

| CFC104 | 5'-CTAGCCCGGGTAC-3' | (SEQ ID NO: 13) |
| CFC105 | 3'-GGGCCCATGGATC-5' | (SEQ ID NO: 14) | were annealed and ligated into the Xba I site, introducing two new restriction sites, Sma I and Kpn I, and destroying the Xba I site. The now unique Xba I site from nucleotide 1–6 in SEQ ID NO:9 and the Ssp I site from nucleotide 1823–1828 in SEQ ID NO:9 were used to obtain a fragment that included the HSZ coding region plus its 5' and 3' regulatory regions. This fragment was cloned into the commercially-available vector pTZ19R (Pharmacia) digested with Xba I and Sma I, yielding plasmid pCC10.

It was desirable to create an altered form of the HSZ gene with a unique restriction endonuclease site at the start of the mature protein, i.e., with the amino terminal signal sequence removed. To accomplish this a DNA fragment was generated using PCR as described in Example 1. Template DNA for the PCR reaction was plasmid pX8m. Oligonucleotide primers for the reaction were:

CFC106 5'-CCACTTCATGACCCATATCCCAGGGCA
    CTT-3' (SEQ ID NO:15)

CFC88 5'-TTCTATCTAGAATGCAGCACCAACAAA
    GGG-3' (SEQ ID NO:16)

The CFC106 (SEQ ID NO:15) oligonucleotide provided the PCR-generated fragment with a BspH I site (underlined), which when digested with BspH I results in a cohesive-end identical to that generated by an Nco I digest. This site was located at the junction of the signal sequence and the mature HSZ coding sequence. The CFC88 (SEQ ID NO:16) oligonucleotide provided the PCR-generated fragment with an Xba I site (underlined) at the translation terminus of the HSZ gene. The BspH I-Xba I fragment (SEQ ID NO:17) obtained by digestion of the PCR-generated fragment, encodes the mature form of HSZ with the addition of a methionine residue at the amino terminus of the protein to permit initiation of translation.

EXAMPLE 6

Construction of Chimeric Genes for Expression of Corn CS, *E. coli* AKIII-M4, and HSZ Proteins in the Embryo and Endosperm of Transformed Corn The following chimeric genes were made for transformation into corn:
globulin 1 promoter/mcts/lysC-M4/globulin 1 3' region
globulin 1 promoter/corn CS coding region/globulin 1 3' region
glutelin 2 promoter/mcts/lysC-M4/NOS 3' region
glutelin 2 promoter/corn CS coding region/10 kD 3' region
10 kD promoter/HSZ coding region/10 kD 3' region
glutelin 2 promoter/HSZ coding region/10 kD 3' region A gene expression cassette employing the 10 kD zein regulatory sequences includes about 925 nucleotides upstream (5') from the translation initiation codon and about 945 nucleotides downstream (3') from the translation stop codon. The entire cassette is flanked by an EcoR I site at the 5' end and BamH I, Sal I and Hind III sites at the 3' end. The DNA sequence of these regulatory regions have been described in the literature [Kirihara et al. (1988) Gene 71:359–370] and DNA fragments carrying these regulatory sequences were obtained from corn genomic DNA via PCR. Between the 5' and 3' regions is a unique Nco I site, which includes the ATG translation initiation codon. The oligonucleotides CFC104 (SEQ ID NO:13) and CFC105 (SEQ ID NO:14) (see Example 5) were inserted at the Xba I site near the 10 kD zein translation stop codon, thus adding a unique Sma I site. An Nco I-Sma I fragment containing the HSZ coding region was isolated from plasmid pCC10 (see Example 5) and inserted into Nco I-Sma I digested 10 kD zein expression cassette creating the chimeric gene: 10 kD promoter/HSZ coding region/10 kD 3' region.

The glutelin 2 promoter was cloned from corn genomic DNA using PCR with primers based on the published sequence [Reina et al. (1990) Nucleic Acids Res. 18:6426–6426]. The promoter fragment includes 1020 nucleotides upstream from the ATG translation start codon. An Nco I site was introduced via PCR at the ATG start site to allow for direct translational fusions. A BamH I site was introduced on the 5' end of the promoter. The 1.02 kb BamH I to Nco I promoter fragment was linked to an Nco I to Hind III fragment carrying the HSZ coding region/10 kD 3' region described above yielding the chimeric gene: glutelin 2 promoter/HSZ coding region/10 kD 3' region in a plasmid designated pML103.

The globulin 1 promoter and 3' sequences were isolated from a Clontech corn genomic DNA library using oligonucleotide probes based on the published sequence of the globulin 1 gene [Kriz et al. (1989) Plant Physiol. 91:636]. The cloned segment includes the promoter fragment extending 1078 nucleotides upstream from the ATG translation start codon, the entire globulin coding sequence including introns and the 3' sequence extending 803 bases from the translational stop. To allow replacement of the globulin 1 coding sequence with other coding sequences an Nco I site was introduced at the ATG start codon, and Kpn I and Xba I sites were introduced following the translational stop codon via PCR to create vector pCC50. There is a second Nco I site within the globulin 1 promoter fragment. The globulin 1 gene cassette is flanked by Hind III sites.

Plant amino acid biosynthetic enzymes are known to be localized in the chloroplasts and therefore are synthesized with a chloroplast targeting signal. Bacterial proteins such as AKIII have no such signal. A chloroplast transit sequence (cts) was therefore fused to the lsyC-M4 coding sequence in the chimeric genes described below. For corn the cts used was based on the the cts of the small subunit of ribulose 1,5-bisphosphate carboxylase from corn [Lebrun et al. (1987) Nucleic Acids Res. 15:4360] and is designated mcts. The oligonucleotides SEQ ID NOS:94–99 were synthesized and used to attach the mcts to lysC-M4.

Oligonucleotides SEQ ID NO:18 and SEQ ID NO:19, which encode the carboxy terminal part of the corn chloroplast targeting signal, were annealed, resulting in Xba I and Nco I compatible ends, purified via polyacrylamide gel electrophoresis, and inserted into Xba I plus Nco I digested pBT492 (see Example 3). The insertion of the correct sequence was verified by DNA sequencing yielding pBT556. Oligonucleotides SEQ ID NO:20 and SEQ ID NO:21, which encode the middle part of the chloroplast targeting signal, were annealed, resulting in Bgl II and Xba I compatible ends, purified via polyacrylamide gel electrophoresis, and inserted into Bgl II and Xba I digested pBT556. The insertion of the correct sequence was verified by DNA sequencing yielding pBT557. Oligonucleotides SEQ ID NO:22 and SEQ ID NO:23, which encode the amino terminal part of the chloroplast targeting signal, were annealed, resulting in Nco I and Afl II compatible ends, purified via polyacrylamide gel electrophoresis, and inserted into Nco I and Afl II digested pBT557. The insertion of the correct sequence was verified by DNA sequencing yielding pBT558. Thus the mcts was fused to the lysC-M4 gene.

To construct the chimeric gene: globulin 1 promoter/mcts/lysC-M4/globulin 1 3' region an Nco I to Hpa I fragment containing the mcts/lysC-M4 coding sequence was isolated from plasmid pBT558 and inserted into Nco I plus Sma I digested pCC50 creating plasmid pBT663.

To construct the chimeric gene: glutelin 2 promoter/mcts/lysC-M4/NOS 3' region the 1.02 kb BamH I to Nco I glutelin 2 promoter fragment described above was linked to the Nco I to Hpa I fragment containing the mcts/lysC-M4 coding sequence described above and to a Sma I to Hind III fragment carrying the NOS 3' region creating.

To construct the chimeric gene: globulin 1 promoter/corn CS coding region/globulin 1 3' region a 1482 base pair BspH I fragment containing the corn CS coding region (see Example 2) was isolated and inserted into an Nco I partial digest of pCC50. A plasmid designated pML157 carried the CS coding region in the proper orientation to create the indicated chimeric gene, as determined via restriction endonuclease digests.

To construct the chimeric gene: glutelin 2 promoter/corn CS coding region/10 kD 3' region the HSZ coding region was removed from pML103 (above) by digestion with Nco I and Xma I and insertion of an oligonucleotide adaptor containing an EcoR I site and Nco I and Xma I sticky ends. The resulting plasmid was digested with Nco I and the 1482 base pair BspH I fragment containing the corn CS coding region (see above and Example 2) was inserted. A plasmid designated pML 159 with the CS coding region in the proper orientation, as determined via restriction endonuclease digests, was obtained, creating the indicated chimeric gene.

A corn CS gene that contained the entire chloroplast targeting signal was constructed by fusing the 5' end of the genomic CS gene to the 3' end of the cDNA. A 697 bp Nco I to Sph I genomic DNA fragment (see SEQ ID NO:26) replaced the analogous Nco I to Sph I fragment in the cDNA. Thus, the first 168 amino acids are encoded by the genomic CS sequence and the coding sequence is interrupted by two introns. The remaining 341 amino acids are encoded by cDNA CS sequence with no further introns, resulting in a protein of 509 amino acids in length (SEQ ID NO:26). A 1750 bp Nco I to BspH I DNA fragment that includes the entire CS coding region was inserted into the corn embryo and endosperm expression cassettes resulting in the chimeric genes globulin 1 promoter/corn CS coding region/globulin 1 3' region in plasmid pFS1198 and glutelin 2 promoter/corn CS coding region/10 kD zein 3' region in plasmid pFS1196, respectively.

EXAMPLE 7

Isolation of the *E. coli* metL Gene and Construction of Chimeric Genes for Expression in the Embryo and Endosperm of Transformed Corn The metL gene of *E. coli* encodes a bifunctional protein, AKII-HDHII; the AK and HDH activities of this enzyme are insensitive to all pathway end-products. The metL gene of *E. coli* has been isolated and sequenced previously [Zakin et al. (1983) J. Biol. Chem. 258:3028–3031]. For the present invention a DNA fragment containing the metL gene was isolated and modified from *E. coli* genomic DNA obtained from strain LE392 using PCR. The following PCR primers were designed and synthesized:

CF23=SEQ ID NO:24: 5'-GAAACCATGG CCAGTGTGAT TGCGCAGGCA

CF24=SEQ ID NO:25: 5'-GAAAGGTACC TFACAACAAC TGT-GCCAGC

These primers add an Nco I site which includes a translation initiation codon at the amino terminus of the AKII-HDHII protein. In order to add the restriction site and additional codon, GCC coding for alanine, was also added to the amino terminus of the protein. The primers also add a Kpn I site immediately following the translation stop codon.

PCR was performed using a Perkin-Elmer Cetus kit according to the instructions of the vendor on a thermocycler manufactured by the same company. The primers were at a concentration of 10 $\mu$M and the thermocycling conditions were:
94° 1 min, 50° 2 min, 72° 8 min for 10 cycles followed by 94° 1 min, 72° 8 min for 30 cycles.
Reactions with four different concentrations of template DNA all yielded the expected 2.4 kb DNA fragment, along with several other smaller fragments. The four PCR reaction mixes were pooled, digested with Nco I and Kpn I and the 2.4 kb fragments were purified and isolated from an agarose gel. The fragment was inserted into a modified pBT430 expression vector (see Example 2) containing a Kpn I site downstream of the Nco I site at the translation initiation codon. DNA was isolated from 8 clones carrying the 2.4 kb fragment in the pBT430 expression vector and transformed into the expression host strain BL21(DE3).

Cultures were grown in TB medium containing ampicillin (100 mg/L) at 37° C. overnight. The cells were collected by centrifugation and resuspended in ⅕th the original culture volume in 50 mM NaCl; 50 mM Tris-Cl, pH 7.5; 1 mM EDTA, and frozen at −20° C., thawed at 37° C. and sonicated, in an ice-water bath, to lyse the cells. The lysate was centrifuged at 4° C. for 5 min at 12,000 rpm. The supernatant was removed and the pellet was resuspended in the above buffer.

The supernatant fractions were assayed for HDH enzyme activities to identify clones expressing functional proteins. HDH activity was assayed as shown below:

HDH ASSAY

| Stock solutions | 1.0 ml | 0.20 ml | Final conc |
|---|---|---|---|
| 0.2M KPO$_4$, pH 7.0 | 500 $\mu$l | 100 $\mu$l | 100 mM |
| 3.7M KCl | 270 $\mu$l | 54 $\mu$l | 1.0 M |
| 0.5M EDTA | 20 $\mu$l | 4 $\mu$l | 10 mM |
| 1.0M MgCl$_2$ | 10 $\mu$l | 2 $\mu$l | 10 mM |
| 2 mM NADPH | 100 $\mu$l | 20 $\mu$l | 0.20 mM |

Make Mixture of above reagents with amounts multiplied by number of assays. Use 0.9 mls of mix for 1 ml assay; 180 $\mu$l of mix for 0.2 ml assay in microtiter dish
Add

| 1.0M ASA in 1.0N HCl | 1 $\mu$l | 0.2 $\mu$l | 1.0 mM |
|---|---|---|---| to ½ the assay mix; remaining ½ lacks ASA to serve as blank

| enzyme extract | 10–100 $\mu$l | 2–20 $\mu$l |
|---|---|---|
| H$_2$0 | to 1.0 ml | to 0.20 ml |

Add enzyme extract last to start reaction. Incubate at ~30° C.; monitor NADPH oxidation at 340 nM. 1 unit oxidizes 1 $\mu$mol NADPH/min at 30° C. in the 1 ml reaction.

Four of eight extracts showed HDH activity well above the control. These four were then assayed for AK activity. AK activity was assayed as shown below:

AK ASSAY

Assay mix (for 12×1.0 mL or 48×0.25 mL assays):

2.5 mls H$_2$O 2.0 mls 4M KOH 2.0 mls 4M NH$_2$OH—HCl 1.0 mls 1M Tris-HCl pH 8.0

0.5 mls 0.2M ATP (121 mg/ml in 0.2M NaOH)

50λ mls 1M MgSO$_4$ pH of assay mix should be 7–8
Each 1.5 ml eppendorf assay tube contains:

|  | MACRO assay | micro assay |
|---|---|---|
| assay mix | 0.64 mls | 0.16 mls |
| 0.2M L-Aspartate | 0.04 mls | 0.01 mls |
| extract | 5–120 µl | 1–30 µl |
| $H_2O$ to total vol. | 0.8 mls | 0.2 mls |
| Assay tubes are incubated at 30° C. for 30–60 min | | |
| Add to develop color; | | |
| $FeCl_3$ reagent | 0.4 mls | 0.1 mls |
| $FeCl_3$ reagent is: | 10% w/w $FeCl_3$ | 50 g |
|  | 3.3% TCA | 15.5 g |
|  | 0.7% HCl | 35 mls HCl |
|  |  | $H_2O$ to 500 mls |

Spin for 2 min in eppendorf centrifuge tube.
Read OD at 540 nm.

Two extracts also had high levels of AK enzyme activity. These two extracts were then tested for inhibition of AK or HDH activity by the pathway end-products, lys, thr and met. Neither the AK nor the HDH activity of the extract from clone 5 was inhibited by 30 mM concentrations of any of the end-products.

The supernatant and pellet fractions of several of the extracts were also analyzed by SDS polyacrylamide gel electrophoresis. In the extract from clone 5, the major protein visible by Coomassie blue staining in both the pellet and supernatant fractions had a molecular weight of about 85 kd, the expected size for AKII-HDHII. The metL gene in plasmid pBT718 from clone 5 was used for all subsequent work.

Plant amino acid biosynthetic enzymes are known to be localized in the chloroplasts and therefore are synthesized with a chloroplast targeting signal. Bacterial proteins have no such signal. A chloroplast transit sequence (cts) was therefore fused to the metL coding sequence in the chimeric genes described below. For corn the cts used was based on the the cts of the small subunit of ribulose 1,5-bisphosphate carboxylase from corn [Lebrun et al. (1987) Nucleic Acids Res. 15:4360] and is designated mcts.

Oligonucleotides SEQ ID NO:18 and SEQ ID NO:19, which encode the carboxy terminal part of the corn chloroplast targeting signal, were annealed, resulting in Xba I and Nco I compatible ends, purified via polyacrylamide gel electrophoresis, and inserted into Xba I plus Nco I digested pBT718. The insertion of the correct sequence was verified by DNA sequencing yielding pB1725. To complete the corn chloroplast targeting signal, pBT725 was digested with Bgl II and Xba I, and a 1.14 kb BamH I to Xba I fragment from pBT580 containing the glutelin 2 promoter plus the amino terminal part of the corn chloroplast targeting signal was inserted creating pBT726.

To construct the chimeric gene:
globulin 1 promoter/mcts/metL/globulin 1 3' region the 2.6 kb Nco I to Kpn I fragment containing the mcts/metL coding sequence was isolated from plasmid pBT726 and inserted into Nco I plus Kpn I digested pCC50 creating plasmid pBT727.

To construct the chimeric gene:
glutelin 2 promoter/mcts/metL/NOS 3' region the 2.6 kb Nco I to Kpn I fragment containing the mcts/metL coding sequence was isolated from plasmid pBT726 and linked to the 1.02 kb BamH I to Nco I glutelin 2 promoter fragment described in Example 6 and to a Kpn I to Hind III fragment carrying the NOS 3' region creating plasmid pBT728.

EXAMPLE 8

Transformation of Corn with Chimeric Genes for Expression of Corn CS and *E. coli* metL in the Embryo and Endosperm Corn was transformed with the chimeric genes:
globulin 1 promoter/mcts/metL/globulin 1 3' region (in pBT727)
globulin 1 promoter/corn CS coding region/globulin 1 3' region (in pFS1198)
glutelin 2 promoter/mcts/metL/NOS 3' region (in pB1728)
glutelin 2 promoter/corn CS coding region/10 kD 3' region (in pFS1196)

The bacterial bar gene from *Streptomyces hygroscopicus* that confers resistance to the herbicide glufosinate [Thompson et al. (1987 The EMBO Journal 6:2519–2523] was used as the selectable marker for corn transformation. The bar gene had its translation codon changed from GTG to ATG for proper translation initiation in plants [De Block et al. (1987) The EMBO Journal 6:2513–2518]. The bar gene was driven by the 35S promoter from Cauliflower Mosaic Virus and uses the termination and polyadenylation signal from the octopine synthase gene from *Agrobacterium tumefaciens*.

Embryogenic callus cultures were initiated from immature embryos (about 1.0 to 1.5 mm) dissected from kernels of a corn line bred for giving a "type II callus" tissue culture response. The embryos were dissected 10 to 12 d after pollination and were placed with the axis-side down and in contact with agarose-solidified N6 medium [Chu et al. (1974) Sci Sin 18:659–668] supplemented with 1.0 mg/L 2,4-D (N6—1.0). The embryos were kept in the dark at 27° C. Friable embryogenic callus consisting of undifferentiated masses of cells with somatic proembryos and somatic embryos borne on suspensor structures proliferated from the scutellum of the immature embryos. Clonal embryogenic calli isolated from individual embryos were identified and sub-cultured on N6—1.0 medium every 2 to 3 weeks.

The particle bombardment method was used to transfer genes to the callus culture cells. A Biolistic PDS-1000/He (BioRAD Laboratories, Hercules, Calif.) was used for these experiments.

Circular plasmid DNA or DNA which had been linearized by restriction endonuclease digestion was precipitated onto the surface of gold particles. DNA from two or three different plasmids, one containing the selectable marker for corn transformation, and one or two containing the chimeric genes for increased methionine accumulation in seeds were co-precipitated. To accomplish this 2.5 µg of each DNA (in water at a concentration of about 1 mg/mL) was added to 25 µL of gold particles (average diameter of 1.0 µm) suspended in water (60 mg of gold per mL). Calcium chloride (25 µL of a 2.5M solution) and spermidine (10 µL of a 0.1M solution) were then added to the gold-DNA suspension as the tube was vortexing for 3 min. The gold particles were centrifuged in a microfuge for 1 sec and the supernatant removed. The gold particles were then resuspended in 1 mL of absolute ethanol, were centrifuged again and the supernatant removed. Finally, the gold particles were resuspended in 25 µL of absolute ethanol and sonicated twice for one sec. Five µL of the DNA-coated gold particles were then loaded on each macro carrier disk and the ethanol was allowed to evaporate away leaving the DNA-covered gold particles dried onto the disk.

Embryogenic callus (from the callus line designated #LH132.5.X, #LH132.6.X, or #LH132.7.X) was arranged in a circular area of about 4 cm in diameter in the center of a 100×20 mm petri dish containing N6—1.0 medium supplemented with 0.25M sorbitol and 0.25M mannitol. The tissue was placed on this medium for 4–6 h prior to bombardment as a pretreatment and remained on the medium during the bombardment procedure. At the end of the 4–6 h pretreatment period, the petri dish containing the tissue was placed in the chamber of the PDS-1000/He. The air in the chamber was then evacuated to a vacuum of 28–29 inch of Hg. The macrocarrier was accelerated with a helium shock wave using a rupture membrane that bursts when the He pressure in the shock tube reaches 1080–1100 psi. The tissue was placed approximately 8 cm from the stopping screen. Five to seven plates of tissue were bombarded with the DNA-coated gold particles. Following bombardment, the callus tissue was transferred to N6—1.0 medium without supplemental sorbitol or mannitol.

Within 3–5 days after bombardment the tissue was transferred to selective medium, N6—1.0 medium that contained 2 mg/L bialaphos. All tissue was transferred to fresh N6—1.0 medium supplemented with bialaphos every 2 weeks. After 6–12 weeks clones of actively growing callus were identified. Callus was then transferred to an MS-based medium that promotes plant regeneration.

What is claimed is:

1. An isolated nucleic acid fragment encoding a plant cystathionine γ-synthase.

2. An isolated nucleic acid fragment encoding a functional plant cystathionine γ-synthase that has the amino acid sequence of SEQ ID NO:27 or any amino acid sequence essentially similar to the amino acid sequence of SEQ ID NO:27 provided that the plant cystathionine γ-synthase corresponding to said sequence is functional.

3. A nucleic acid fragment essentially similar to that of SEQ ID NO:1, said fragment encoding a functional plant cystathionine γ-synthase.

4. A nucleic acid fragment essentially similar to that of SEQ ID NO:26, said fragment comprising a genomic DNA fragment comprising the coding and non-coding sequences of a functional plant cystathionine γ-synthase.

5. The isolated nucleic acid fragment of claim 1 encoding a corn cystathionine γ-synthase.

6. An isolated nucleic acid fragment comprising:
   (a) an isolated nucleic acid fragment encoding a plant cystathionine γ-synthase; and
   (b) a second nucleic acid fragment encoding aspartokinase which is insensitive to end-product inhibition.

7. The nucleic acid fragment of claim 6, wherein at least one of the following conditions are met:
   (a) the isolated nucleic acid fragment encoding a plant cystathionine γ-synthase is from corn;
   (b) the second nucleic acid fragment comprises a nucleotide sequence encoding a lysine-insensitive variant of E. Coli AKIII that is essentially similar to the sequence shown in SEQ ID NO:4 and further characterized in that at least one of the following conditions is met:
      (1) the amino acid at position 318 is an amino acid other than methionine; or
      (2) the amino acid at position 352 is an amino acid other than threonine.

8. An isolated nucleic acid fragment comprising
   (a) the isolated nucleic acid fragment of claim 1; and
   (b) a second nucleic acid fragment encoding a bi-functional protein with aspartokinase and homoserine dehydrogenase activities wherein both the aspartokinase and homoserine dehydrogenase activities are insensitive to end-product inhibition.

9. The nucleic acid fragment of claim 8, wherein at least one of the following conditions are met:
   (a) the isolated nucleic acid fragment is from corn
   (b) the second nucleic acid fragment comprises a nucleotide sequence essentially similar to the E. coli metL gene.

10. A chimeric gene wherein the nucleic acid fragment of claim 1 is operably linked to a seed specific regulatory sequence.

11. A nucleic acid fragment comprising:
    (a) the chimeric gene of claim 10 and
    (b) a second chimeric gene comprising a nucleotide sequence encoding aspartokinase which is insensitive to end-product inhibition, wherein said nucleotide sequence is operably linked to a plant chloroplast transit sequence and to a seed-specific regulatory sequence.

12. A nucleic acid fragment comprising:
    (a) the chimeric gene of claim 10 and
    (b) a second chimeric gene comprising a nucleotide sequence encoding a bi-functional protein with aspartokinase and homoserine dehydrogenase activities, wherein both the aspartokinase and homoserine dehydrogenase activities are insensitive to end-product inhibition, and wherein said nucleotide sequence is operably linked to a plant chloroplast transit sequence and to a seed-specific regulatory sequence.

13. A plant comprising in its genome the chimeric gene of claim 10 or the nucleic acid fragment of claim 11 or the nucleic acid fragment of claim 12.

14. Seeds obtained from the plant of claim 13.

15. A method for increasing the methionine content of the seeds of plants comprising:
    (a) transforming plant cells with the chimeric gene of claim 10 or the nucleic acid fragment of claim 11 or the nucleic acid fragment of claim 12;
    (b) growing fertile mature plants from the transformed plant cells obtained from step (a) to obtain seeds; and
    (c) selecting from the seeds of step (b) those seeds containing increased levels of methionine compared to untransformed seeds.

16. A plant comprising in its genome:
    (a) a nucleic acid fragment wherein said fragment comprises the nucleic acid fragment of claim 11 or the nucleic acid fragment of claim 12 or the chimeric gene of claim 10, and
    (b) a chimeric gene comprising a nucleotide sequence encoding a methionine-rich protein, wherein the weight percent methionine is at least 15%, and wherein said nucleotide sequence is operably linked to a seed-specific regulatory sequence.

17. A nucleic acid fragment comprising:
    (a) a first nucleic acid fragment comprising the nucleic acid fragment of claim 11 or the nucleic acid fragment of claim 12 or the chimeric gene of claim 10, and
    (b) a chimeric gene comprising a nucleotide sequence encoding a methionine-rich protein, wherein the weight percent methionine is at least 15%, and wherein said nucleotide sequence is operably linked to a seed-specific regulatory sequence.

18. A plant comprising in its genome the nucleic acid fragment of claim 17.

19. Seeds obtained from the plant of claim 18.

20. Seeds obtained from the plant of claim 16.

21. A method for increasing the methionine content of the seeds of plants comprising:

(a) transforming plant cells with the nucleic acid fragment of claim 17;

(b) growing fertile mature plants from the transformed plant cells obtained from step (a); and (c) selecting from the seeds of step (b) those seeds containing increased levels of methionine compared to untransformed seeds.

22. A chimeric gene comprising the nucleic acid fragment of claim 2 operably linked to a regulatory sequence that causes expression in microbial cells.

23. A method of producing plant cystathionine γ-synthase comprising:

(a) transforming a microbial host cell with the chimeric gene of claim 22;

(b) growing the transformed microbial host cell obtained from step (a), resulting in the expression of plant cystathionine γ-synthase protein.

24. A chimeric gene wherein the nucleic acid fragment of claim 1 is operably linked to a seed specific regulatory sequence.

25. A nucleic acid fragrnent comprising (a) the chimeric gene of claim 24 and (b) a second chimeric gene comprising a nucleotide sequence encoding aspartokinase which is insensitive to end-product inhibition, wherein said nucleotide sequence is operably linked to a plant chloroplast transit sequence and to a seed-specific regulatory sequence.

26. A nucleic acid fragment comprising (a) the chimeric gene of claim 24 and (b) a second chimeric gene comprising a nucleotide sequence encoding a bi-functional protein with aspartokinase and homoserine dehydrogenase activities, wherein both the aspartokinase and homoserine dehydrogenase activities are insensitive to end-product inhibition, and wherein said nucleotide sequence is operably linked to a plant cliloroplast transit sequence and to a seed-specific regulatory sequence.

27. A plant comprising in its genonie the chimeric gene of claim 24 or the nucleic acid fragment of claim 25 or the nucleic acid fragment of claim 26.

28. Seeds obtained from the plant of claim 27.

29. A method for increasing the methionine content of the seeds of plants comprising:

(a) transforming plant cells with the chimeric gene of claim 24 or the nucleic acid fragment of claim 25 or the nucleic acid fragment of claim 26;

(b) growing fertile mature plants from the transformed plant cells obtained from step (a) to obtain seeds; and (c) selecting from the seeds of step (b) those seeds containing increased levels of methionine compared to untransformed seeds.

30. A plant comprising in its genome (a) a nucleic acid fragment wherein said fragment comprises the nucleic acid fragment of claim 24 or the nucleic acid fragment of claim 25 or the nucleic acid fragment of claim 26; and (b) a chimeric gene comprising a nucleotide sequence encoding a methionine-rich protein, wherein the weight percent methionine is at least 15%, and wherein said nucleotide sequence is operably linked to a seed-specific regulatory sequence.

31. A nucleic acid fragment comprising (a) a first nucleic acid fragment comprising the nucleic acid fragment of the chimeric gene of claim 24 or the nucleic acid fragment of claim 25 or the nucleic acid fragment of claim 26; and (b) a chimeric gene comprising a nucleotide sequence encoding a methionine-rich protein, wherein the weight percent methionine is at least 15%, and wherein said nucleotide sequence is operably linked to a seed-specific regulatory sequence.

32. A plant comprising in its genome the nucleic acid fragment of claim 31.

33. Seeds obtained from the plant of claim 32.

34. A method for increasing the methionine content of the seeds of plants comprising:

(a) transforming plant cells with the nucleic acid fragment of claim 31;

(b) growing fertile mature plants from the transformed plant cells obtained from step (a); and (c) selecting from the seeds of step (b) those seeds containing increased levels of methionine compared to untransformed seeds.

35. A chimeric gene comprising the nucleic acid fragment of claim 23 operably linked to a regulatory sequence that causes expression in microbial cells.

36. A method for producing plant cystathionine γ-synthase comprising:

(a) transforming a microbial host cell with the chimeric gene of claim 35;

(b) growing the transformed microbial host cell obtained from step (a), resulting in the expression of plant cystathionine γ-synthase protein.

37. Seeds obtained from the plant of claim 30.

* * * * *

```
                              SEQUENCE LISTING (1) GENERAL INFORMATION:

(iii) NUMBER OF SEQUENCES:  27

(2) INFORMATION FOR SEQ ID NO:1:

(i) SEQUENCE CHARACTERISTICS:
           (A) LENGTH:  1639 base pairs
           (B) TYPE:  nucleic acid
           (C) STRANDEDNESS:  double
           (D) TOPOLOGY:  linear (ii) MOLECULE TYPE:  cDNA (ix) FEATURE:
           (A) NAME/KEY:  CDS
           (B) LOCATION:  2..1441

(xi) SEQUENCE DESCRIPTION:  SEQ ID NO:1:

G AAT TCC GGC TCG AAG CCG CCG CGA CCG AAC GAG CGA AGC GTC CCT              46
  Asn Ser Gly Ser Lys Pro Pro Arg Pro Asn Glu Arg Ser Val Pro
   1               5                  10                  15

TCC CGC GCC GAC GCC GAA ACC CTA GCT CCT CTT ACG CCA TGG CCA CCG            94
Ser Arg Ala Asp Ala Glu Thr Leu Ala Pro Leu Thr Pro Trp Pro Pro
                 20                  25                  30

TGT CGC TCA CTC CGC AGG CGG TCT TCT CCA CCG AGT CCG GCG GCG CCC           142
Cys Arg Ser Leu Arg Arg Arg Ser Ser Pro Pro Ser Pro Ala Ala Pro
             35                  40                  45

TGG CCT CTG CCA CCA TCC TCC GCT TCC CGC CAA ACT TCG TCC GCC TCC           190
Trp Pro Leu Pro Pro Ser Ser Ala Ser Arg Gln Thr Ser Ser Ala Ser
         50                  55                  60

GCG GCG GCG GAT GTC AGC GCA ATT CCT AAC GCT AAG GTT GCG CAG CCG           238
Ala Ala Ala Asp Val Ser Ala Ile Pro Asn Ala Lys Val Ala Gln Pro
     65                  70                  75

TCC GCC GTC GTA TTG GCC GAG CGT AAC CTG CTC GGC TCC GAC GCC AGC           286
Ser Ala Val Val Leu Ala Glu Arg Asn Leu Leu Gly Ser Asp Ala Ser
 80                  85                  90                  95

CTC GCC GTC CAC GCG GGG GAG AGG CTG GGA AGA AGG ATA GCC ACG GAT           334
Leu Ala Val His Ala Gly Glu Arg Leu Gly Arg Arg Ile Ala Thr Asp
                100                 105                 110

GCT ATC ACC ACG CCG GTA GTG AAC ACG TCG GCC TAC TGG TTC AAC AAC           382
Ala Ile Thr Thr Pro Val Val Asn Thr Ser Ala Tyr Trp Phe Asn Asn
            115                 120                 125

TCG CAA GAG CTA ATC GAC TTT AAG GAG GGG AGG CAT GCT AGC TTC GAG           430
Ser Gln Glu Leu Ile Asp Phe Lys Glu Gly Arg His Ala Ser Phe Glu
        130                 135                 140

TAT GGG AGG TAT GGG AAC CCG ACC ACG GAG GCA TTA GAG AAG AAG ATG           478
Tyr Gly Arg Tyr Gly Asn Pro Thr Thr Glu Ala Leu Glu Lys Lys Met
    145                 150                 155
```

```
AGC GCA CTG GAG AAA GCA GAG TCC ACC GTG TTT GTG GCG TCA GGG ATG        526
Ser Ala Leu Glu Lys Ala Glu Ser Thr Val Phe Val Ala Ser Gly Met
160             165                 170                 175

TAT GCA GCT GTG GCT ATG CTC AGC GCA CTT GTC CCT GCT GGT GGG CAC        574
Tyr Ala Ala Val Ala Met Leu Ser Ala Leu Val Pro Ala Gly Gly His
                180                 185                 190

ATT GTG ACC ACC ACG GAT TGC TAC CGC AAG ACA AGG ATT TAC ATG GAA        622
Ile Val Thr Thr Thr Asp Cys Tyr Arg Lys Thr Arg Ile Tyr Met Glu
            195                 200                 205

AAT GAG CTC CCT AAG AGG GGA ATT TCG ATG ACT GTC ATT AGG CCT GCT        670
Asn Glu Leu Pro Lys Arg Gly Ile Ser Met Thr Val Ile Arg Pro Ala
        210                 215                 220

GAC ATG GAT GCT CTC CAA AAT GCC TTG GAC AAC AAT AAT GTA TCT CTT        718
Asp Met Asp Ala Leu Gln Asn Ala Leu Asp Asn Asn Asn Val Ser Leu
    225                 230                 235

TTC TTC ACG GAG ACT CCT ACA AAT CCA TTT CTC AGA TGC ATT GAT ATT        766
Phe Phe Thr Glu Thr Pro Thr Asn Pro Phe Leu Arg Cys Ile Asp Ile
240                 245                 250                 255

GAA CAT GTA TCA AAT ATG TGC CAT AGC AAG GGA GCG TTG CTT TGT ATT        814
Glu His Val Ser Asn Met Cys His Ser Lys Gly Ala Leu Leu Cys Ile
                260                 265                 270

GAC AGT ACT TTC GCG TCA CCT ATC AAT CAG AAG GCA TTA ACT TTA GGT        862
Asp Ser Thr Phe Ala Ser Pro Ile Asn Gln Lys Ala Leu Thr Leu Gly
            275                 280                 285

GCT GAC CTA GTT ATT CAT TCT GCA ACG AAG TAC ATT GCT GGA CAC AAT        910
Ala Asp Leu Val Ile His Ser Ala Thr Lys Tyr Ile Ala Gly His Asn
        290                 295                 300

GAT GTT ATT GGA GGA TGC GTC AGT GGC AGA GAT GAG TTA GTT TCC AAA        958
Asp Val Ile Gly Gly Cys Val Ser Gly Arg Asp Glu Leu Val Ser Lys
    305                 310                 315

GTT CGT ATT TAC CAC CAT GTA GTT GGT GGT GTT CTA AAC CCG AAT GCT       1006
Val Arg Ile Tyr His His Val Val Gly Gly Val Leu Asn Pro Asn Ala
320                 325                 330                 335

GCG TAC CTT ATC CTT CGA GGT ATG AAG ACA CTG CAT CTC CGT GTG CAA       1054
Ala Tyr Leu Ile Leu Arg Gly Met Lys Thr Leu His Leu Arg Val Gln
                340                 345                 350

TGT CAG AAC GAC ACT GCT CTT CGG ATG GCC CAG TTT TTA GAG GAG CAT       1102
Cys Gln Asn Asp Thr Ala Leu Arg Met Ala Gln Phe Leu Glu Glu His
            355                 360                 365

CCA AAG ATT GCT CGT GTC TAC TAT CCT GGC TTG CCA AGT CAC CCT GAA       1150
Pro Lys Ile Ala Arg Val Tyr Tyr Pro Gly Leu Pro Ser His Pro Glu
        370                 375                 380

CAT CAC ATT GCC AAG AGT CAA ATG ACT GGC TTT GGC GGT GTT GTT AGT       1198
His His Ile Ala Lys Ser Gln Met Thr Gly Phe Gly Gly Val Val Ser
    385                 390                 395

TTT GAG GTT GCT GGA GAC TTT GAT GCT ACG AGG AAA TTC ATT GAT TCT       1246
Phe Glu Val Ala Gly Asp Phe Asp Ala Thr Arg Lys Phe Ile Asp Ser
400                 405                 410                 415

GTT AAA ATA CCC TAT CAT GCG CCT TCT TTT GGA GGC TGT GAG AGC ATA       1294
Val Lys Ile Pro Tyr His Ala Pro Ser Phe Gly Gly Cys Glu Ser Ile
                420                 425                 430

ATT GAT CAG CCT GCC ATC ATG TCC TAC TGG GAT TCA AAG GAG CAG CGG       1342
Ile Asp Gln Pro Ala Ile Met Ser Tyr Trp Asp Ser Lys Glu Gln Arg
            435                 440                 445

GAC ATC TAC GGG ATC AAG GAC AAC CTG ATC AGG TTC AGC ATT GGT GTG       1390
Asp Ile Tyr Gly Ile Lys Asp Asn Leu Ile Arg Phe Ser Ile Gly Val
        450                 455                 460

GAG GAT TTC GAG GAT CTT AAG AAC GAT CTC GTG CAG GCC CTC GAG AAG       1438
Glu Asp Phe Glu Asp Leu Lys Asn Asp Leu Val Gln Ala Leu Glu Lys
    465                 470                 475
```

-continued

```
ATC TAA GCACTCTAAT CAGTTTGTAT TGACAAAATC ATGAGGTGAT GGCTGTCTTG        1494
Ile
480

GATCTTGTCA AGATCTGTGA CAATGATATG AGCTGATGAC TGCGAATAAG                1544

TTCTCTTTTG CTTATTTTAT CCGTCAAATT CAAAAAAAAA AAAAAAAAA                 1594

AAAAAAAAAA AAAAAAAAAA AAAAAAAAAA AAAAAAAAC TCGAG                      1639
```

(2) INFORMATION FOR SEQ ID NO:2:

(i) SEQUENCE CHARACTERISTICS:
        (A) LENGTH: 14 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

```
AATTCATGAG TGCA                                                         14
```

(2) INFORMATION FOR SEQ ID NO:3:

(i) SEQUENCE CHARACTERISTICS:
        (A) LENGTH: 14 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

```
AATTTGCACT CATG                                                         14
```

(2) INFORMATION FOR SEQ ID NO:4:

(i) SEQUENCE CHARACTERISTICS:
        (A) LENGTH: 1350 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1350

(xi) SEQUENCE DESCRIPTION: SEQ ID NO:4:

```
ATG GCT GAA ATT GTT GTC TCC AAA TTT GGC GGT ACC AGC GTA GCT GAT        48
Met Ala Glu Ile Val Val Ser Lys Phe Gly Gly Thr Ser Val Ala Asp
 1               5                  10                  15

TTT GAC GCC ATG AAC CGC AGC GCT GAT ATT GTG CTT TCT GAT GCC AAC        96
Phe Asp Ala Met Asn Arg Ser Ala Asp Ile Val Leu Ser Asp Ala Asn
                20                  25                  30

GTG CGT TTA GTT GTC CTC TCG GCT TCT GCT GGT ATC ACT AAT CTG CTG       144
Val Arg Leu Val Val Leu Ser Ala Ser Ala Gly Ile Thr Asn Leu Leu
         35                  40                  45

GTC GCT TTA GCT GAA GGA CTG GAA CCT GGC GAG CGA TTC GAA AAA CTC       192
Val Ala Leu Ala Glu Gly Leu Glu Pro Gly Glu Arg Phe Glu Lys Leu
     50                  55                  60

GAC GCT ATC CGC AAC ATC CAG TTT GCC ATT CTG GAA CGT CTG CGT TAC       240
Asp Ala Ile Arg Asn Ile Gln Phe Ala Ile Leu Glu Arg Leu Arg Tyr
 65                  70                  75                  80

CCG AAC GTT ATC CGT GAA GAG ATT GAA CGT CTG CTG GAG AAC ATT ACT       288
Pro Asn Val Ile Arg Glu Glu Ile Glu Arg Leu Leu Glu Asn Ile Thr
                 85                  90                  95
```

```
GTT CTG GCA GAA GCG GCG GCG CTG GCA ACG TCT CCG GCG CTG ACA GAT        336
Val Leu Ala Glu Ala Ala Ala Leu Ala Thr Ser Pro Ala Leu Thr Asp
            100                 105                 110

GAG CTG GTC AGC CAC GGC GAG CTG ATG TCG ACC CTG CTG TTT GTT GAG        384
Glu Leu Val Ser His Gly Glu Leu Met Ser Thr Leu Leu Phe Val Glu
            115                 120                 125

ATC CTG CGC GAA CGC GAT GTT CAG GCA CAG TGG TTT GAT GTA CGT AAA        432
Ile Leu Arg Glu Arg Asp Val Gln Ala Gln Trp Phe Asp Val Arg Lys
    130                 135                 140

GTG ATG CGT ACC AAC GAC CGA TTT GGT CGT GCA GAG CCA GAT ATA GCC        480
Val Met Arg Thr Asn Asp Arg Phe Gly Arg Ala Glu Pro Asp Ile Ala
145                 150                 155                 160

GCG CTG GCG GAA CTG GCC GCG CTG CAG CTG CTC CCA CGT CTC AAT GAA        528
Ala Leu Ala Glu Leu Ala Ala Leu Gln Leu Leu Pro Arg Leu Asn Glu
            165                 170                 175

GGC TTA GTG ATC ACC CAG GGA TTT ATC GGT AGC GAA AAT AAA GGT CGT        576
Gly Leu Val Ile Thr Gln Gly Phe Ile Gly Ser Glu Asn Lys Gly Arg
            180                 185                 190

ACA ACG ACG CTT GGC CGT GGA GGC AGC GAT TAT ACG GCA GCC TTG CTG        624
Thr Thr Thr Leu Gly Arg Gly Gly Ser Asp Tyr Thr Ala Ala Leu Leu
            195                 200                 205

GCG GAG GCT TTA CAC GCA TCT CGT GTT GAT ATC TGG ACC GAC GTC CCG        672
Ala Glu Ala Leu His Ala Ser Arg Val Asp Ile Trp Thr Asp Val Pro
210                 215                 220

GGC ATC TAC ACC ACC GAT CCA CGC GTA GTT TCC GCA GCA AAA CGC ATT        720
Gly Ile Tyr Thr Thr Asp Pro Arg Val Val Ser Ala Ala Lys Arg Ile
225                 230                 235                 240

GAT GAA ATC GCG TTT GCC GAA GCG GCA GAG ATG GCA ACT TTT GGT GCA        768
Asp Glu Ile Ala Phe Ala Glu Ala Ala Glu Met Ala Thr Phe Gly Ala
                245                 250                 255

AAA GTA CTG CAT CCG GCA ACG TTG CTA CCC GCA GTA CGC AGC GAT ATC        816
Lys Val Leu His Pro Ala Thr Leu Leu Pro Ala Val Arg Ser Asp Ile
            260                 265                 270

CCG GTC TTT GTC GGC TCC AGC AAA GAC CCA CGC GCA GGT GGT ACG CTG        864
Pro Val Phe Val Gly Ser Ser Lys Asp Pro Arg Ala Gly Gly Thr Leu
            275                 280                 285

GTG TGC AAT AAA ACT GAA AAT CCG CCG CTG TTC CGC GCT CTG GCG CTT        912
Val Cys Asn Lys Thr Glu Asn Pro Pro Leu Phe Arg Ala Leu Ala Leu
            290                 295                 300

CGT CGC AAT CAG ACT CTG CTC ACT TTG CAC AGC CTG AAT ATG CTG CAT        960
Arg Arg Asn Gln Thr Leu Leu Thr Leu His Ser Leu Asn Met Leu His
305                 310                 315                 320

TCT CGC GGT TTC CTC GCG GAA GTT TTC GGC ATC CTC GCG CGG CAT AAT       1008
Ser Arg Gly Phe Leu Ala Glu Val Phe Gly Ile Leu Ala Arg His Asn
                325                 330                 335

ATT TCG GTA GAC TTA ATC ACC ACG TCA GAA GTG AGC GTG GCA TTA ACC       1056
Ile Ser Val Asp Leu Ile Thr Thr Ser Glu Val Ser Val Ala Leu Thr
            340                 345                 350

CTT GAT ACC ACC GGT TCA ACC TCC ACT GGC GAT ACG TTG CTG ACG CAA       1104
Leu Asp Thr Thr Gly Ser Thr Ser Thr Gly Asp Thr Leu Leu Thr Gln
            355                 360                 365

TCT CTG CTG ATG GAG CTT TCC GCA CTG TGT CGG GTG GAG GTG GAA GAA       1152
Ser Leu Leu Met Glu Leu Ser Ala Leu Cys Arg Val Glu Val Glu Glu
            370                 375                 380

GGT CTG GCG CTG GTC GCG TTG ATT GGC AAT GAC CTG TCA AAA GCC TGC       1200
Gly Leu Ala Leu Val Ala Leu Ile Gly Asn Asp Leu Ser Lys Ala Cys
385                 390                 395                 400

GCC GTT GGC AAA GAG GTA TTC GGC GTA CTG GAA CCG TTC AAC ATT CGC       1248
Ala Val Gly Lys Glu Val Phe Gly Val Leu Glu Pro Phe Asn Ile Arg
                405                 410                 415
```

```
ATG ATT TGT TAT GGC GCA TCC AGC CAT AAC CTG TGC TTC CTG GTG CCC    1296
Met Ile Cys Tyr Gly Ala Ser Ser His Asn Leu Cys Phe Leu Val Pro
        420                 425                 430

GGC GAA GAT GCC GAG CAG GTG GTG CAA AAA CTG CAT AGT AAT TTG TTT    1344
Gly Glu Asp Ala Glu Gln Val Val Gln Lys Leu His Ser Asn Leu Phe
        435                 440                 445

GAG TAA                                                             1350
Glu *
450

(2) INFORMATION FOR SEQ ID NO:5:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GATCCATGGC TGAAATTGTT GTCTCCAAAT TTGGCG                              36

(2) INFORMATION FOR SEQ ID NO:6:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GTACCGCCAA ATTTGGAGAC AACAATTTCA GCCATG                              36

(2) INFORMATION FOR SEQ ID NO:7:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ATGGCAGCCA AGATGCTTGC ATTGTTCGCT                                     30

(2) INFORMATION FOR SEQ ID NO:8:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GAATGCAGCA CCAACAAAGG GTTGCTGTAA                                     30

(2) INFORMATION FOR SEQ ID NO:9:

(i) SEQUENCE CHARACTERISTICS:
        (A) LENGTH: 2123 base pairs
        (B) TYPE: nucleic acid
        (C) STRANDEDNESS: single
```

43

-continued (D) TOPOLOGY: linear (ii) MOLECULE TYPE: DNA (genomic)

(ix) FEATURE:
        (A) NAME/KEY: CDS
        (B) LOCATION: 1113..1385

(xi) SEQUENCE DESCRIPTION: SEQ ID NO:9:

```
TCTAGAGCCT ATTACCATCT CTACTCACGG GTCGTAGAGG TGGTGAGGTA           50

GGCTACAGCT GGTGACAATC CTACTCACCC TTTGTAATCC TCTACGGCTC          100

TACGCGTAGT TAATTGGTTA GATGTCAACC CCCTCTCTAA GTGGCAGTAG          150

TGGGCTTGGT TATACCTGCT AGTGCCTGGG GATGTTCTAT TTTTCTAGTA          200

GTGCTTGATC AAACATTGCA TAGTTTGACT TGGGACAAAC TGTCTGATAT          250

ATATATATAT TTTTGGGCAG AGGGAGCAGT AAGAACTTAT TTAGAAATGT          300

AATCATTTGT TAAAAAGGT TTAATTTTGC TGCTTTCTTT CGTTAATGTT           350

GTTTTCACAT TAGATTTTCT TTGTGTTATA TACACTGGAT ACATACAAAT          400

TCAGTTGCAG TAGTCTCTTA ATCCACATCA GCTAGGCATA CTTTAGCAAA          450

AGCAAATTAC ACAAATCTAG TGTGCCTGTC GTCACATTCT CAATAAACTC          500

GTCATGTTTT ACTAAAAGTA CCTTTTCGAA GCATCATATT AATCCGAAAA          550

CAGTTAGGGA AGTCTCCAAA TCTGACCAAA TGCCAAGTCA TCGTCCAGCT          600

TATCAGCATC CAACTTTCAG TTTCGCATGT GCTAGAAATT GTTTTTCATC          650

TACATGGCCA TTGTTGACTG CATGCATCTA TAAATAGGAC CTAGACGATC          700

AATCGCAATC GCATATCCAC TATTCTCTAG GAAGCAAGGG AATCACATCG          750

CC                                                              752
```

| | | |
|---|---|---|
| ATG GCA GCC AAG ATG TTT GCA TTG TTT GCG CTC CTA GCT CTT TGT | | 797 |
| Met Ala Ala Lys Met Phe Ala Leu Phe Ala Leu Leu Ala Leu Cys | | |
|     -20              -15             -10 | | |
| GCA ACC GCC ACT AGT GCT ACC CAT ATC CCA GGG CAC TTG TCA CCA | | 842 |
| Ala Thr Ala Thr Ser Ala Thr His Ile Pro Gly His Leu Ser Pro | | |
|   -5              1             5 | | |
| CTA CTG ATG CCA TTG GCT ACC ATG AAC CCA TGG ATG CAG TAC TGC | | 887 |
| Leu Leu Met Pro Leu Ala Thr Met Asn Pro Trp Met Gln Tyr Cys | | |
| 10              15             20 | | |
| ATG AAG CAA CAG GGG GTT GCC AAC TTG TTA GCG TGG CCG ACC CTG | | 932 |
| Met Lys Gln Gln Gly Val Ala Asn Leu Leu Ala Trp Pro Thr Leu | | |
| 25              30             35 | | |
| ATG CTG CAG CAA CTG TTG GCC TCA CCG CTT CAG CAG TGC CAG ATG | | 977 |
| Met Leu Gln Gln Leu Leu Ala Ser Pro Leu Gln Gln Cys Gln Met | | |
| 40              45             50 | | |
| CCA ATG ATG ATG CCG GGT ATG ATG CCA CCG ATG ACG ATG ATG CCG | | 1022 |
| Pro Met Met Met Pro Gly Met Met Pro Pro Met Thr Met Met Pro | | |
| 55              60             65 | | |
| ATG CCG AGT ATG ATG CCA TCG ATG ATG GTG CCG ACT ATG ATG TCA | | 1067 |
| Met Pro Ser Met Met Pro Ser Met Met Val Pro Thr Met Met Ser | | |
| 70              75             80 | | |
| CCA ATG ACG ATG GCT AGT ATG ATG CCG CCG ATG ATG ATG CCA AGC | | 1112 |
| Pro Met Thr Met Ala Ser Met Met Pro Pro Met Met Met Pro Ser | | |
| 85              90             95 | | |
| ATG ATT TCA CCA ATG ACG ATG CCG AGT ATG ATG CCT TCG ATG ATA | | 1157 |
| Met Ile Ser Pro Met Thr Met Pro Ser Met Met Pro Ser Met Ile | | |
| 100            105            110 | | |
| ATG CCG ACC ATG ATG TCA CCA ATG ATT ATG CCG AGT ATG ATG CCA | | 1202 |
| Met Pro Thr Met Met Ser Pro Met Ile Met Pro Ser Met Met Pro | | |
| 115            120            125 | | |

-continued

```
CCA ATG ATG ATG CCG AGC ATG GTG TCA CCA ATG ATG ATG CCA AAC    1247
Pro Met Met Met Pro Ser Met Val Ser Pro Met Met Met Pro Asn
130                 135                 140

ATG ATG ACA GTG CCA CAA TGT TAC TCT GGT TCT ATC TCA CAC ATT    1292
Met Met Thr Val Pro Gln Cys Tyr Ser Gly Ser Ile Ser His Ile
145                 150                 155

ATA CAA CAA CAA CAA TTA CCA TTC ATG TTC AGC CCC ACA GCC ATG    1337
Ile Gln Gln Gln Gln Leu Pro Phe Met Phe Ser Pro Thr Ala Met
160                 165                 170

GCG ATC CCA CCC ATG TTC TTA CAG CAG CCC TTT GTT GGT GCT GCA    1382
Ala Ile Pro Pro Met Phe Leu Gln Gln Pro Phe Val Gly Ala Ala
175                 180                 185

TTC TAG   ATCTAGATAT AA                                        1400
Phe
190

GCATTTGTGT AGTACCCAAT AATGAAGTCG GCATGCCATC GCATACGACT          1450

CATTGTTTAG GAATAAAACA AGCTAATAAT GACTTTCTC TCATTATAAC           1500

TTATATCTCT CCATGTCTGT TTGTGTGTTT GTAATGTCTG TTAATCTTAG          1550

TAGATTATAT TGTATATATA ACCATGTATT CTCTCCATTC CAAATTATAG          1600

GTCTTGCATT TCAAGATAAA TAGTTTTAAC CATACCTAGA CATTATGTAT          1650

ATATAGGCGG CTTAACAAAA GCTATGTACT CAGTAAAATC AAAACGACTT          1700

ACAATTTAAA ATTAGAAAG TACATTTTTA TTAATAGACT AGGTGAGTAC           1750

TTGTGCGTTG CAACGGGAAC ATATAATAAC ATAATAACTT ATATACAAAA          1800

TGTATCTTAT ATTGTTATAA AAAATATTTC ATAATCCATT TGTAATCCTA          1850

GTCATACATA AATTTTGTTA TTTTAATTTA GTTGTTTCAC TACTACATTG          1900

CAACCATTAG TATCATGCAG ACTTCGATAT ATGCCAAGAT TTGCATGGTC          1950

TCATCATTGA AGAGCACATG TCACACCTGC CGGTAGAAGT TCTCTCGTAC          2000

ATTGTCAGTC ATCAGGTACG CACCACCATA CACGCTTGCT TAAACAAAAA          2050

AACAAGTGTA TGTGTTTGCG AAGAGAATTA AGACAGGCAG ACACAAAGCT          2100

ACCCGACGAT GGCGAGTCGG TCA                                      2123
```

(2) INFORMATION FOR SEQ ID NO:10:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
ATGAACCCTT GGATGCA                                               17
```

(2) INFORMATION FOR SEQ ID NO:11:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

```
CCCACAGCAA TGGCGAT                                               17
```

(2) INFORMATION FOR SEQ ID NO:12:

(i) SEQUENCE CHARACTERISTICS:
        (A) LENGTH: 639 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..635

(xi) SEQUENCE DESCRIPTION: SEQ ID NO:12:

```
CC ATG GCA GCC AAG ATG TTT GCA TTG TTT GCG CTC CTA GCT CTT TGT      47
   Met Ala Ala Lys Met Phe Ala Leu Phe Ala Leu Leu Ala Leu Cys
   -20             -15                 -10

GCA ACC GCC ACT AGT GCT ACC CAT ATC CCA GGG CAC TTG TCA CCA         92
Ala Thr Ala Thr Ser Ala Thr His Ile Pro Gly His Leu Ser Pro
 -5              1               5

CTA CTG ATG CCA TTG GCT ACC ATG AAC CCT TGG ATG CAG TAC TGC        137
Leu Leu Met Pro Leu Ala Thr Met Asn Pro Trp Met Gln Tyr Cys
 10              15                  20

ATG AAG CAA CAG GGG GTT GCC AAC TTG TTA GCG TGG CCG ACC CTG        182
Met Lys Gln Gln Gly Val Ala Asn Leu Leu Ala Trp Pro Thr Leu
 25              30                  35

ATG CTG CAG CAA CTG TTG GCC TCA CCG CTT CAG CAG TGC CAG ATG        227
Met Leu Gln Gln Leu Leu Ala Ser Pro Leu Gln Gln Cys Gln Met
 40              45                  50

CCA ATG ATG ATG CCG GGT ATG ATG CCA CCG ATG ACG ATG ATG CCG        272
Pro Met Met Met Pro Gly Met Met Pro Pro Met Thr Met Met Pro
 55              60                  65

ATG CCG AGT ATG ATG CCA TCG ATG ATG GTG CCG ACT ATG ATG TCA        317
Met Pro Ser Met Met Pro Ser Met Met Val Pro Thr Met Met Ser
 70              75                  80

CCA ATG ACG ATG GCT AGT ATG ATG CCG CCG ATG ATG ATG CCA AGC        362
Pro Met Thr Met Ala Ser Met Met Pro Pro Met Met Met Pro Ser
 85              90                  95

ATG ATT TCA CCA ATG ACG ATG CCG AGT ATG ATG CCT TCG ATG ATA        407
Met Ile Ser Pro Met Thr Met Pro Ser Met Met Pro Ser Met Ile
100             105                 110

ATG CCG ACC ATG ATG TCA CCA ATG ATT ATG CCG AGT ATG ATG CCA        452
Met Pro Thr Met Met Ser Pro Met Ile Met Pro Ser Met Met Pro
115             120                 125

CCA ATG ATG ATG CCG AGC ATG GTG TCA CCA ATG ATG ATG CCA AAC        497
Pro Met Met Met Pro Ser Met Val Ser Pro Met Met Met Pro Asn
130             135                 140

ATG ATG ACA GTG CCA CAA TGT TAC TCT GGT TCT ATC TCA CAC ATT        542
Met Met Thr Val Pro Gln Cys Tyr Ser Gly Ser Ile Ser His Ile
145             150                 155

ATA CAA CAA CAA CAA TTA CCA TTC ATG TTC AGC CCC ACA GCA ATG        587
Ile Gln Gln Gln Gln Leu Pro Phe Met Phe Ser Pro Thr Ala Met
160             165                 170

GCG ATC CCA CCC ATG TTC TTA CAG CAG CCC TTT GTT GGT GCT GCA        632
Ala Ile Pro Pro Met Phe Leu Gln Gln Pro Phe Val Gly Ala Ala
175             180                 185

TTC TAG A                                                          639
Phe
190
```

(2) INFORMATION FOR SEQ ID NO:13:

(i) SEQUENCE CHARACTERISTICS:
    (A) LENGTH: 13 bases
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:13:

CTAGCCCGGG TAC                                                    13

(2) INFORMATION FOR SEQ ID NO:14:

(i) SEQUENCE CHARACTERISTICS:
        (A) LENGTH: 13 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

CTAGGTACCC GGG                                                    13

(2) INFORMATION FOR SEQ ID NO:15:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

CCACTTCATG ACCCATATCC CAGGGCACTT                                  30

(2) INFORMATION FOR SEQ ID NO:16:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

TTCTATCTAG AATGCAGCAC CAACAAAGGG                                  30

(2) INFORMATION FOR SEQ ID NO:17:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..575

(xi) SEQUENCE DESCRIPTION: SEQ ID NO:17:

TC ATG ACC CAT ATC CCA GGG CAC TTG TCA CCA CTA CTG ATG CCA TTG    47
   Met Thr His Ile Pro Gly His Leu Ser Pro Leu Leu Met Pro Leu
     5                  10                  15

GCT ACC ATG AAC CCT TGG ATG CAG TAC TGC ATG AAG CAA CAG GGG       92

```
Ala Thr Met Asn Pro Trp Met Gln Tyr Cys Met Lys Gln Gln Gly
 20                  25                  30

GTT GCC AAC TTG TTA GCG TGG CCG ACC CTG ATG CTG CAG CAA CTG         137
Val Ala Asn Leu Leu Ala Trp Pro Thr Leu Met Leu Gln Gln Leu
 35                  40                  45

TTG GCC TCA CCG CTT CAG CAG TGC CAG ATG CCA ATG ATG ATG CCG         182
Leu Ala Ser Pro Leu Gln Gln Cys Gln Met Pro Met Met Met Pro
 50                  55                  60

GGT ATG ATG CCA CCG ATG ACG ATG ATG CCG ATG CCG AGT ATG ATG         227
Gly Met Met Pro Pro Met Thr Met Met Pro Met Pro Ser Met Met
 65                  70                  75

CCA TCG ATG ATG GTG CCG ACT ATG ATG TCA CCA ATG ACG ATG GCT         272
Pro Ser Met Met Val Pro Thr Met Met Ser Pro Met Thr Met Ala
 80                  85                  90

AGT ATG ATG CCG CCG ATG ATG ATG CCA AGC ATG ATT TCA CCA ATG         317
Ser Met Met Pro Pro Met Met Met Pro Ser Met Ile Ser Pro Met
 95                  100                 105

ACG ATG CCG AGT ATG ATG CCT TCG ATG ATA ATG CCG ACC ATG ATG         362
Thr Met Pro Ser Met Met Pro Ser Met Ile Met Pro Thr Met Met
 110                 115                 120

TCA CCA ATG ATT ATG CCG AGT ATG ATG CCA CCA ATG ATG ATG CCG         407
Ser Pro Met Ile Met Pro Ser Met Met Pro Pro Met Met Met Pro
 125                 130                 135

AGC ATG GTG TCA CCA ATG ATG ATG CCA AAC ATG ATG ACA GTG CCA         452
Ser Met Val Ser Pro Met Met Met Pro Asn Met Met Thr Val Pro
 140                 145                 150

CAA TGT TAC TCT GGT TCT ATC TCA CAC ATT ATA CAA CAA CAA CAA         497
Gln Cys Tyr Ser Gly Ser Ile Ser His Ile Ile Gln Gln Gln Gln
 155                 160                 165

TTA CCA TTC ATG TTC AGC CCC ACA GCA ATG GCG ATC CCA CCC ATG         542
Leu Pro Phe Met Phe Ser Pro Thr Ala Met Ala Ile Pro Pro Met
 170                 175                 180

TTC TTA CAG CAG CCC TTT GTT GGT GCT GCA TTC TAG A                   579
Phe Leu Gln Gln Pro Phe Val Gly Ala Ala Phe
 185                 190

(2) INFORMATION FOR SEQ ID NO:18:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CTAGAAGCCT CGGCAACGTC AGCAACGGCG AAGAATCCG GTG                       43

(2) INFORMATION FOR SEQ ID NO:19:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CATGCACCGG ATTCTTCCGC CGTTGCTGAC GTTGCCGAGG CTT                      43

(2) INFORMATION FOR SEQ ID NO:20:
```

(i) SEQUENCE CHARACTERISTICS:
            (A) LENGTH:  55 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:20:

GATCCCATGG CGCCCCTTAA GTCCACCGCC AGCCTCCCCG TCGCCCGCCG CTCCT                55

(2) INFORMATION FOR SEQ ID NO:21:

(i) SEQUENCE CHARACTERISTICS:
            (A) LENGTH:  55 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:21:

CTAGAGGAGC GGCGGGCGAC GGGGAGGCTG GCGGTGGACT TAAGGGGCGC CATGG                55

(2) INFORMATION FOR SEQ ID NO:22:

(i) SEQUENCE CHARACTERISTICS:
            (A) LENGTH:  59 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:22:

CATGGCGCCC ACCGTGATGA TGGCCTCGTC GGCCACCGCC GTCGCTCCGT TCCAGGGGC            59

(2) INFORMATION FOR SEQ ID NO:23:

(i) SEQUENCE CHARACTERISTICS:
            (A) LENGTH:  59 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:23:

TTAAGCCCCT GGAACGGAGC GACGGCGGTG GCCGACGAGG CCATCATCAC GGTGGGCGC            59

(2) INFORMATION FOR SEQ ID NO:24:

(i) SEQUENCE CHARACTERISTICS:
            (A) LENGTH:  30 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:24:

GAAACCATGG CCAGTGTGAT TGCGCAGGCA                                            30

(2) INFORMATION FOR SEQ ID NO:25:

(i) SEQUENCE CHARACTERISTICS:
            (A) LENGTH:  29 base pairs
            (B) TYPE:  nucleic acid
            (C) STRANDEDNESS:  single
            (D) TOPOLOGY:  linear (ii) MOLECULE TYPE: DNA (genomic)

(xi) SEQUENCE DESCRIPTION: SEQ ID NO:25:

| GAAAGGTACC TTACAACAAC TGTGCCAGC | 29 |

(2) INFORMATION FOR SEQ ID NO:26:

(i) SEQUENCE CHARACTERISTICS:
        (A) LENGTH: 3639 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

| TCTAGATTAC ATAATACACC TAATAATCTT GTGTTGTTTG TTTACTTCTC AACTTATTTA | 60 |
| AGTTGGATTA TATTCCATCT TTTCTTTTTT ATTTGTCTGT TTTAGTTAAA AATGAACTAA | 120 |
| CAAACGACAA ATATTCGAGA ACGAGATAGT ATAATCTATA GGATAATCAG ACATGTCCTT | 180 |
| AGAGGGTGTT TGTTTAGAAT TATAATATGT ATAGAATATA TAATCCAACA AATTTTGAAC | 240 |
| TAACAAGTTT AAAATTTGAT AGATTATATA ATCTGGGCAC ATTATAATCC TAAACAAACA | 300 |
| CCATCTTAGT AATTTTTTAT TTAGTGCTCC GTTTGGATGT GAAGAAGATG GAGTTGAATA | 360 |
| CCAAATCATG TATGATACTG AAATGAGATG TAATTTTAAT TCTATTGTTT GGATGTCGTT | 420 |
| GAATTGGAGT TTGAAGTTAT GCGGTCTAAT TTTACGCAAT ACCGAGATGA GACTTTATAC | 480 |
| TAGGAGAGGG GTTTCTAGTT ATAGCCTAAT TCTAAAGAAT TGAGTCTCTA TTTCCAAATC | 540 |
| TTAATTTTAT GCAACTAAAC AACACAATTT AGAAAAACTG TTTTCAATTT CTTATTCTGT | 600 |
| GCTCCAAACG AGGTGGAGTA TTTAGAAGTA GATAAGCGCC TCTGCTGCAC GAAGCGATGA | 660 |
| ACGCACTCTG ACGGTCTTGC CACTACAAAT AAGCCGCACC GCATTTCGGA AGGCCACGCG | 720 |
| ACCGCCACCT CCCCGAAGCT GCCGCGACCG ATCGAGCGAA GCGTCGCTCC CCGCGCCGCC | 780 |
| GCCAAAACCC TAGCTTCTCC TACTCCATGG CCACTGTCTC GCTCACCCCG CAGGCTGTCT | 840 |
| TCTCCACGGA GTCCGGTGGC GCCCTGGCCT CTGCTACCAT CCTCCGCTTT CCGCCAAACT | 900 |
| TTGTCCGCCA GCTTAGCACC AAGGCACGCC GCAACTGCAG CAACATCGGC GTCGCGCAGA | 960 |
| TCGTCGCCGC CGCGTGGTCC GACTGCCCCG CCGCTCGCCC CCACTTAGGC GGCGGCGGCC | 1020 |
| GCCGCGCCCG CGGCGTGGCC TCCTCCCACG CCGCGGCTGC ATCGGCCGCC GCCGCCGCCT | 1080 |
| CCGCGGCGGC GGAGGTCAGC GCAATTCCCA ACGCTAAGGT TGCGCAACCG TCCGCCGTCG | 1140 |
| TCTTGGCCGA GCGTAACCTG CTCGGCTCCG ACGCCAGCCT CGCCGTCCAC GCGGGTACCC | 1200 |
| TACCCTGCTA GCTCGTCTCT TTACTGTAAG ATCTAGGTTC TATGCTTTTT TCCCCTTTCG | 1260 |
| ATGATTCCTT TGTGGCTTTG CTGCCTTTTT ATCTGAAACA GGGGAGAGGC TGGGAAGAAG | 1320 |
| GATCGCCACG GATGCGATCA CCACACCGGT AGTGAACACG TCGGCCTACT GGTTCAACAA | 1380 |
| CTCGCAAGAG CTAATCGACT TTAAGGTAGT GAATATTCGT GCTTGCTCTT GTCTAATTTG | 1440 |
| ACGGATGTGA GTTTTGACGC CGAAATATTA AGTTTTATCT GTTCCTTAGG AGGGGAGGCA | 1500 |
| TGCTAGCTTC GAGTATGGGA GGTATGGGAA CCCGACCACG GAGGCATTAG AGAAGAAGAT | 1560 |
| GAGGTGATGC TCGATAGTGG AAATGTCGGC ACCCTGTTGG TTGCATTTGG CTGGAGGCTA | 1620 |
| AACAGTTGCG TGTTCTCATG GTGCAGCGCA CTGGAGAAAG CAGAGTCCAC AGTGTTCGTG | 1680 |
| GCATCGGGGA TGTATGCAGC TGCGGCTATG CTCAGTGCAC TTGTTCCGGC TGGTGGGCAC | 1740 |
| ATTGTGACCA CCACGGATTG CTACCGGAAA ACAAGGATTT ACATGGAAAC TGAGCTCCCC | 1800 |

```
AAGAGGGGAA TTTCGGTAAT ACCATGCGAT CTTTTAAGCT CTACTTGTTT TTAGAACGGG     1860

ACATCTGCTA TCACTATTGG TTGTCTTCCT GTCACTGTGC TACAGTAGTG GGTCTACAAT     1920

GAACTTGCTC TTATTCAGTT AAAATTACTC TGTCGTGTTG TCCTTATCTA GCTAATAGTC     1980

TCTACAAAGT TCAGTTACTT CAGCATAGCC AATAGGAGTA GCATAACTAC TGCAGGGTAT     2040

ATGAACAATA TCCTTTGCAG TAGCTGTTGG GAGTACACAG TACAGTATGG CTTCAGACTT     2100

TATTCTTTGT ACTGCATTGG GTGAAGCCAC ATAGGGTTTG CCGAGTGCAC GTGCACCAGG     2160

GAAAAAACAA TTTCTACTTT TCTAGTGATT AAAAACTAAA TTTTACCACT CATGCACACC     2220

CTAATTTTTA ATTAGAGAAG ATTTTCAATA CATGTGTATA TTGAAATGTC AAGTGTGCAC     2280

TCGGATTCTC CGGCCTCTAG CTTCGCCCGA CTGCAATGTC AATAGGATTG CTATCTGTA     2340

AAGGATTTAA GTAGAACTGC TTGTGGTAAT AAATTTTAGG ATCCCTCACA ATAAGATTTA     2400

TTATATAATC ACACCATCTA CCAGTTGAAA TGCAGTGAGA GCACTTTGTG AGTTGTATAC     2460

CAATGTTTCT CACGCTTCAC TTAGCATGTG ATACTGTTTA TGCTCAGATG ACTGTCATTA     2520

GGCCTGCTGA CATGGATGCT CTACAAAATG CGTTGGACAA CAATAATGTG AGTGTGGTAT     2580

CATTTCCATT GCCCCTGATC GTGGTAAAAA ACATACATTA ATACATTTGC AAATGTAGCC     2640

TAACCTTATG GCCATGTCAG GTATCTCTTT TCTTCACGGA GACTCCCACA AATCCATTTC     2700

TCAGATGCAT TGATATTGAA CATGTATCAA ATATGTGCCA TAGCAAGGGA GCGTTGCTTT     2760

GTATCGACAG TACTTTTGCC TCCCCTATCA ATCAGAAGGC ACTGACTTTA GGCGCTGACC     2820

TAGTTATTCA TTCTGCAACA AAGTACATTG CTGGACACAA CGATGTGAGT TGATATACTG     2880

AACCCCATCT CCCCTCATTA AAGTTATGTG TTTGCACATT GCACTAACTA GTACTTCAAC     2940

TTCCCAGGTT ATTGGAGGAT GCGTCAGTGG CAGAGATGAG TTGGTTTCCA AAGTCCGTAT     3000

TTATCACCAT GTGGTTGGTG GTGTTCTAAA CCCGGTAAGT TTAGATTGTT AAAGTTTTGT     3060

TTCCATTTAT TTCATCTTCC TTGCACAGGT TGTATGTATT TACAGATTCC CATAGTTACA     3120

AGCTTCTATT TTTATAGGTA GAAAATCGTG TAATTTTCTT TAGTAGCATA TGTTTAGGTT     3180

AGAAAAATAA TTTGCTTTCT CTGAGTATCA CAAACCGCAT CCAGTTCTCT GTTACATGAA     3240

CTAGAATTCT GGTTCTGGAA AGGAAGAAAT AGGATATGTT CTGTGCACTG CAATATATAT     3300

CTAATCATTA ATCCGGAGCT TTATGTCACA GACTCACAGG CCAGGCTACC ACTTTATGAA     3360

ATATTCCAAA TTATGCTTGT CTCAAAATGG AATGACTCAT GTTGTACTCT GTTCCAACGT     3420

TTTCAAATCA TGACTAGGAT TCTAGTTGCC CGGACACCGA CTAGGTGATT AATCGTGACT     3480

AGGCATTGAC TAGTCACGAT TAGTTTTGAG CTAGTCGAAC TTATCAACAA CTTGTTCCAG     3540

GCAATATATT GCAGTACTAT GCCTTATTGA TTGGGTATAT AAATGAATTT TAGCACACAG     3600

ATAGAGCAGA AGTAAGACAA ATTAACACAA AGTTCTAGA                           3639
```

(2) INFORMATION FOR SEQ ID NO:27:

(i) SEQUENCE CHARACTERISTICS:
        (A) LENGTH: 509 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

```
Met Ala Thr Val Ser Leu Thr Pro Gln Ala Val Phe Ser Thr Glu Ser
 1               5                  10                  15

Gly Gly Ala Leu Ala Ser Ala Thr Ile Leu Arg Phe Pro Pro Asn Phe
            20                  25                  30
```

-continued

```
Val Arg Gln Leu Ser Thr Lys Ala Arg Arg Asn Cys Ser Asn Ile Gly
         35                  40                  45
Val Ala Gln Ile Val Ala Ala Ala Trp Ser Asp Cys Pro Ala Ala Arg
         50                  55                  60
Pro His Leu Gly Gly Gly Arg Arg Ala Arg Gly Val Ala Ser Ser
 65                  70                  75                  80
His Ala Ala Ala Ala Ser Ala Ala Ala Ala Ser Ala Ala Ala Glu
                 85                  90                  95
Val Ser Ala Ile Pro Asn Ala Lys Val Ala Gln Pro Ser Ala Val Val
                100                 105                 110
Leu Ala Glu Arg Asn Leu Leu Gly Ser Asp Ala Ser Leu Ala Val His
                115                 120                 125
Ala Gly Glu Arg Leu Gly Arg Arg Ile Ala Thr Asp Ala Ile Thr Thr
                130                 135                 140
Pro Val Val Asn Thr Ser Ala Tyr Trp Phe Asn Asn Ser Gln Glu Leu
145                 150                 155                 160
Ile Asp Phe Lys Glu Gly Arg His Ala Ser Phe Glu Tyr Gly Arg Tyr
                165                 170                 175
Gly Asn Pro Thr Thr Glu Ala Leu Glu Lys Lys Met Ser Ala Leu Glu
                180                 185                 190
Lys Ala Glu Ser Thr Val Phe Val Ala Ser Gly Met Tyr Ala Ala Val
                195                 200                 205
Ala Met Leu Ser Ala Leu Val Pro Ala Gly His Ile Val Thr Thr
                210                 215                 220
Thr Asp Cys Tyr Arg Lys Thr Arg Ile Tyr Met Glu Asn Glu Leu Pro
225                 230                 235                 240
Lys Arg Gly Ile Ser Met Thr Val Ile Arg Pro Ala Asp Met Asp Ala
                245                 250                 255
Leu Gln Asn Ala Leu Asp Asn Asn Val Ser Leu Phe Phe Thr Glu
                260                 265                 270
Thr Pro Thr Asn Pro Phe Leu Arg Cys Ile Asp Ile Glu His Val Ser
                275                 280                 285
Asn Met Cys His Ser Lys Gly Ala Leu Leu Cys Ile Asp Ser Thr Phe
                290                 295                 300
Ala Ser Pro Ile Asn Gln Lys Ala Leu Thr Leu Gly Ala Asp Leu Val
305                 310                 315                 320
Ile His Ser Ala Thr Lys Tyr Ile Ala Gly His Asn Asp Val Ile Gly
                325                 330                 335
Gly Cys Val Ser Gly Arg Asp Glu Leu Val Ser Lys Val Arg Ile Tyr
                340                 345                 350
His His Val Val Gly Gly Val Leu Asn Pro Asn Ala Ala Tyr Leu Ile
                355                 360                 365
Leu Arg Gly Met Lys Thr Leu His Leu Arg Val Gln Cys Gln Asn Asp
                370                 375                 380
Thr Ala Leu Arg Met Ala Gln Phe Leu Glu Glu His Pro Lys Ile Ala
385                 390                 395                 400
Arg Val Tyr Tyr Pro Gly Leu Pro Ser His Pro Glu His Ile Ala
                405                 410                 415
Lys Ser Gln Met Thr Gly Phe Gly Gly Val Val Ser Phe Glu Val Ala
                420                 425                 430
Gly Asp Phe Asp Ala Thr Arg Lys Phe Ile Asp Ser Val Lys Ile Pro
                435                 440                 445
Tyr His Ala Pro Ser Phe Gly Gly Cys Glu Ser Ile Ile Asp Gln Pro
450                 455                 460
```

```
Ala Ile Met Ser Tyr Trp Asp Ser Lys Glu Gln Arg Asp Ile Tyr Gly
465                 470                 475                 480

Ile Lys Asp Asn Leu Ile Arg Phe Ser Ile Gly Val Glu Asp Phe Glu
                485                 490                 495

Asp Leu Lys Asn Asp Leu Val Gln Ala Leu Glu Lys Ile
            500                 505
```